(12) United States Patent
Trinklein et al.

(10) Patent No.: US 9,006,405 B2
(45) Date of Patent: Apr. 14, 2015

(54) MODIFIED RENILLA LUCIFERASE NUCLEIC ACIDS AND METHODS OF USE

(75) Inventors: Nathan D. Trinklein, San Carlos, CA (US); Shelley Force Aldred, Hayward, CA (US)

(73) Assignee: SwitchGear Genomics, Inc., Menlo Park, CA (US)

( * ) Notice: Subject to any disclaimer, the term of this patent is extended or adjusted under 35 U.S.C. 154(b) by 690 days.

(21) Appl. No.: 13/134,121

(22) Filed: May 27, 2011

(65) Prior Publication Data

US 2012/0035077 A1    Feb. 9, 2012

Related U.S. Application Data

(60) Provisional application No. 61/397,340, filed on Jun. 10, 2010.

(51) Int. Cl.
C12Q 1/66    (2006.01)
C12N 15/52   (2006.01)
C12N 9/02    (2006.01)

(52) U.S. Cl.
CPC ............. *C12N 9/0069* (2013.01); *C12Q 1/66* (2013.01)

(58) Field of Classification Search
None
See application file for complete search history.

(56) References Cited

U.S. PATENT DOCUMENTS

| | | | |
|---|---|---|---|
| 5,418,155 A | 5/1995 | Cormier et al. | |
| 2002/0090320 A1* | 7/2002 | Burow et al. | 422/64 |
| 2006/0024808 A1* | 2/2006 | Darzins et al. | 435/195 |
| 2006/0068395 A1 | 3/2006 | Wood et al. | |
| 2007/0161031 A1 | 7/2007 | Trinklein et al. | |
| 2008/0220983 A1 | 9/2008 | Trinklein et al. | |
| 2009/0018031 A1 | 1/2009 | Trinklein et al. | |
| 2011/0065100 A1 | 3/2011 | Aldred et al. | |

FOREIGN PATENT DOCUMENTS

| | | | |
|---|---|---|---|
| WO | WO 92/15673 | 9/1992 | |
| WO | WO 02/16944 | * 2/2002 | G01N 33/53 |

OTHER PUBLICATIONS

The International Bureau of WIPO, PCT International Preliminary Report on Patentability (Oct. 12, 2012) for PCT/US2011/000963, filed May 27, 2011.
Subramanian, C. et al., "The *Arabidopsis* repressor of light signaling, COP1, is regulated by nuclear exclusion: Mutational analysis by bioluminescence resonance energy transfer," Proc. Natl. Acad. Sci. USA, 101 (Apr. 27, 2004), pp. 6798-6802.
Subramanian, C. et al., "A suite of tools and application notes for in vivo protein interaction assays using bioluminescence resonance energy transfer (BRET)," Plant J., 48 (Oct. 2006), pp. 138-152.
Higgins, Desmond G. et al., "CLUSTAL: a package for performing multiple sequence alignment on a microcomputer," Gene, 73 (1988), pp. 237-244.
Communication Pursuant to Rule 70(2) and 70(2A) EPC dated Nov. 15, 2013 for European Patent Application 11792764.0.
Promega Corporation: Technical Manual: pGL4 Luciferase Repoerter Vectors, Mar. 1, 2009.
Shefira, A. S. et al., "Factors modulating expression of *Renilla* luciferase from control plasmids used in luciferase reporter gene assay," Analytical Biochem. 396:167 Jan. 15, 2010.
XP-002714578: Synthetic *Renilla* luciferase reporter vector pGL4.83 [hRlucP/Puro], complete sequence; www.ncbi.nlm.nih.gov/nuccore/DQ188847, Aug. 10, 2013.

* cited by examiner

*Primary Examiner* — Reza Ghafoorian
(74) *Attorney, Agent, or Firm* — Storella, P.C.

(57) ABSTRACT

This invention provides modified nucleotide sequences encoding luciferase that have greater expression than wild type luciferase.

41 Claims, 25 Drawing Sheets

FIGURE 1: Results from the functional screen of Renilla codon variants

FIG. 3

| SEQ ID NO | Name | Sequence | Note |
|---|---|---|---|
| SEQ ID NO. 1 | RenS protein | MASKVYDPEQRKRMITGPQWWARCKQMNVLDSFINYYDSEKH AENAVIFLHGNAASSYLWRHVVPHIEPVARCIIPDLIGMGKSGKS GNGSYRLLDHYKYLTAWFELLNLPKKIIFVGHDWGACLAFHYSYE HQDKIKAIVHAESVVDVIESWDEWPDIEEDIALIKSEEGEKMVLEN NFFVETMLPSKIMRKLEPEEFAAYLEPFKEKGEVRRPTLSWPREIP LVKGGKPDVVQIVRNYNAYLRASDDLPKMFIESDPGFFSNAIVEG AKKFPNTEFVKVKGLHFSQEDAPDEMGKYIKSFVERVLKNEQ | optimized Renilla without Pest sequence |
| SEQ ID NO. 2 | RenS | AAGCTTGGCATTCCGGTACTGTTGGTAAAGCCACCATGGCTTC CAAGGTGTACGACCCGGAGCAGCGCAAGAGGATGATCACCG GCCCTCAGTGGTGGGCTCGGTGCAAGCAGATGAACGTGCTCG ACTCCTTCATCAACTACTACGACAGCGAGAAACATGCGGAGAA CGCCGTGATCTTCCTCCACGGCAACGCCGCTTCCTCCTACCTGT GGCGCCACGTCGTGCCCCACATCGAGCCCGTCGCCCGGTGCAT CATCCCTGATCTGATCGGGATGGGGAAGAGCGGGAAGAGCG GCAACGGCAGCTACCGCCTGCTCGACCACTACAAGTACCTCAC CGCCTGGTTCGAGCTGCTGAACCTCCCCAAGAAGATCATCTTT GTGGGCCACGACTGGGGCGCTTGTCTCGCTTTTCACTACTCCT ACGAGCACCAGGATAAGATCAAGGCTATCGTGCATGCTGAGA GCGTCGTGGACGTGATCGAGTCCTGGGACGAGTGGCCCGATA TCGAGGAGGATATTGCTCTGATCAAGTCCGAGGAGGGCGAGA AGATGGTCCTGGAGAATAACTTCTTCGTGGAGACTATGCTGCC TAGCAAGATCATGCGCAAGCTGGAGCCCGAGGAGTTCGCTGC TTACCTGGAGCCCTTCAAGGAGAAGGGCGAGGTCAGAAGACC AACCCTCAGCTGGCCTCGGGAGATCCCTCTGGTCAAGGGCGG GAAGCCGGACGTGGTGCAGATCGTCCGGAACTACAACGCCTA CCTGCGCGCCAGCGACGACCTGCCTAAGATGTTCATCGAGTCC GACCCCGGCTTCTTCAGCAACGCTATCGTGGAGGGCGCCAAG AAGTTCCCCAACACCGAGTTCGTGAAGGTGAAGGGCCTCCACT TCTCCCAAGAGGACGCCCCTGATGAGATGGGGAAGTACATCA AGAGCTTCGTCGAGCGCGTCCTCAAGAACGAGCAGTAATTCTA GA | optimized Renilla without Pest sequence |
| SEQ ID NO. 3 | RenSP protein | MASKVYDPEQRKRMITGPQWWARCKQMNVLDSFINYYDSEKH AENAVIFLHGNAASSYLWRHVVPHIEPVARCIIPDLIGMGKSGKS GNGSYRLLDHYKYLTAWFELLNLPKKIIFVGHDWGACLAFHYSYE HQDKIKAIVHAESVVDVIESWDEWPDIEEDIALIKSEEGEKMVLEN NFFVETMLPSKIMRKLEPEEFAAYLEPFKEKGEVRRPTLSWPREIP LVKGGKPDVVQIVRNYNAYLRASDDLPKMFIESDPGFFSNAIVEG AKKFPNTEFVKVKGLHFSQEDAPDEMGKYIKSFVERVLKNEQNS HGFPPEVEEQAAGTLPMSCAQESGMDRHPAACASARINV | optimized Renilla with Pest sequence |

| SEQ ID NO | Name | Sequence | Note |
|---|---|---|---|
| SEQ ID NO. 4 | RenSP | AAGCTTGGCATTCCGGTACTGTTGGTAAAGCCACCATGGCTTC CAAGGTGTACGACCCGGAGCAGCGCAAGAGGATGATCACCG GCCCTCAGTGGTGGGCTCGGTGCAAGCAGATGAACGTGCTCG ACTCCTTCATCAACTACTACGACAGCGAGAAACATGCGGAGAA CGCCGTGATCTTCCTCCACGGCAACGCCGCTTCCTCCTACCTGT GGCGCCACGTCGTGCCCCACATCGAGCCCGTCGCCCGGTGCAT CATCCCTGATCTGATCGGGATGGGGAAGAGCGGGAAGAGCG GCAACGGCAGCTACCGCCTGCTCGACCACTACAAGTACCTCAC CGCCTGGTTCGAGCTGCTGAACCTCCCCAAGAAGATCATCTTT GTGGGCCACGACTGGGGCGCTTGTCTCGCTTTTCACTACTCCT ACGAGCACCAGGATAAGATCAAGGCTATCGTGCATGCTGAGA GCGTCGTGGACGTGATCGAGTCCTGGGACGAGTGGCCCGATA TCGAGGAGGATATTGCTCTGATCAAGTCCGAGGAGGGCGAGA AGATGGTCCTGGAGAATAACTTCTTCGTGGAGACTATGCTGCC TAGCAAGATCATGCGCAAGCTGGAGCCCGAGGAGTTCGCTGC TTACCTGGAGCCCTTCAAGGAGAAGGGCGAGGTCAGAAGACC AACCCTCAGCTGGCCTCGGGAGATCCCTCTGGTCAAGGGCGG GAAGCCGGACGTGGTGCAGATCGTCCGGAACTACAACGCCTA CCTGCGCGCCAGCGACGACCTGCCTAAGATGTTCATCGAGTCC GACCCCGGCTTCTTCAGCAACGCTATCGTGGAGGGCGCCAAG AAGTTCCCCAACACCGAGTTCGTGAAGGTGAAGGGCCTCCACT TCTCCCAAGAGGACGCCCCTGATGAGATGGGGAAGTACATCA AGAGCTTCGTCGAGCGCGTCCTCAAGAACGAGCAGAATTCTCA CGGCTTCCCTCCCGAGGTGGAGGAGCAGGCCGCCGGCACCCT GCCCATGAGCTGCGCCCAGGAGAGCGGCATGGATAGACACCC TGCTGCTTGCGCCAGCGCCAGGATCAACGTCTAATCTAGA | optimized Renilla with Pest sequence |

FIG. 3 (cont.)

| SEQ ID NO | Name | Sequence | Note |
|---|---|---|---|
| SEQ ID NO. 5 | pLightSwitch_prom | GGCCTAACTGGCCGGTACCTGAGCTCTTACGCGTGCTAGCCCG GGCTCGAGATCTGCGATCTAAGTAAGCTTAACTAAGTAAGGCA TTCCGGTACTGTTGGTAAAGCCACCATGGCTTCCAAGGTGTAC GACCCGGAGCAGCGCAAGAGGATGATCACCGGCCCTCAGTGG TGGGCTCGGTGCAAGCAGATGAACGTGCTCGACTCCTTCATCA ACTACTACGACAGCGAGAAACATGCGGAGAACGCCGTGATCT TCCTCCACGGCAACGCCGCTTCCTCCTACCTGTGGCGCCACGTC GTGCCCCACATCGAGCCCGTCGCCCGGTGCATCATCCCTGATC TGATCGGGATGGGGAAGAGCGGGAAGAGCGGCAACGGCAGC TACCGCCTGCTCGACCACTACAAGTACCTCACCGCCTGGTTCG AGCTGCTGAACCTCCCCAAGAAGATCATCTTTGTGGGCCACGA CTGGGGCGCTTGTCTCGCTTTTCACTACTCCTACGAGCACCAG GATAAGATCAAGGCTATCGTGCATGCTGAGAGCGTCGTGGAC GTGATCGAGTCCTGGGACGAGTGGCCCGATATCGAGGAGGAT ATTGCTCTGATCAAGTCCGAGGAGGGCGAGAAGATGGTCCTG GAGAATAACTTCTTCGTGGAGACTATGCTGCCTAGCAAGATCA TGCGCAAGCTGGAGCCCGAGGAGTTCGCTGCTTACCTGGAGC CCTTCAAGGAGAAGGGCGAGGTCAGAAGACCAACCCCTCAGCT GGCCTCGGGAGATCCCTCTGGTCAAGGGCGGGAAGCCGGAC GTGGTGCAGATCGTCCGGAACTACAACGCCTACCTGCGCGCCA GCGACGACCTGCCTAAGATGTTCATCGAGTCCGACCCCGGCTT CTTCAGCAACGCTATCGTGGAGGGCGCCAAGAAGTTCCCCAAC ACCGAGTTCGTGAAGGTGAAGGGCCTCCACTTCTCCCAAGAG GACGCCCCTGATGAGATGGGGAAGTACATCAAGAGCTTCGTC GAGCGCGTCCTCAAGAACGAGCAGAATTCTCACGGCTTCCCTC CCGAGGTGGAGGAGCAGGCCGCCGGCACCCTGCCCATGAGCT GCGCCCAGGAGAGCGGCATGGATAGACACCCTGCTGCTTGCG CCAGCGCCAGGATCAACGTCTAATCTAGAGTCGGGGCGGCCG GCCGCTTCGAGCAGACATGATAAGATACATTGATGAGTTTGGA CAAACCACAACTAGAATGCAGTGAAAAAAATGCTTTATTTGTG AAATTTGTGATGCTATTGCTTTATTTGTAACCATTATAAGCTGC AATAAACAAGTTAACAACAACAATTGCATTCATTTTATGTTTCA GGTTCAGGGGGAGGTGTGGGAGGTTTTTTAAAGCAAGTAAAA CCTCTACAAATGTGGTAAAATCGATAAGGATCCGTCGACCGAT GCCCTTGAGAGCCTTCAACCCAGTCAGCTCCTTCCGGTGGGCG CGGGGCATGACTATCGTCGCCGCACTTATGACTGTCTTCTTTAT CATGCAACTCGTAGGACAGGTGCCGGCAGCGCTCTTCCGCTTC CTCGCTCACTGACTCGCTGCGCTCGGTCGTTCGGCTGCGGCGA GCGGTATCAGCTCACTCAAAGGCGGTAATACGGTTATCCACAG AATCAGGGGATAACGCAGGAAAGAACATGTGAGCAAAAGGC CAGCAAAAGGCCAGGAACCGTAAAAAGGCCGCGTTGCTGGCG TTTTTCCATAGGCTCCGCCCCCCTGACGAGCATCACAAAAATCG ACGCTCAAGTCAGAGGTGGCGAAACCCGACAGGACTATAAAG ATACCAGGCGTTTCCCCCTGGAAGCTCCCTCGTGCGCTCTCCTG TTCCGACCCTGCCGCTTACCGGATACCTGTCCGCCTTTCTCCCTT CGGGAAGCGTGGCGCTTTCTCATAGCTCACGCTGTAGGTATCT CAGTTCGGTGTAGGTCGTTCGCTCCAAGCTGGGCTGTGTGCAC GAACCCCCCGTTCAGCCCGACCGCTGCGCCTTATCCGGTAACT ATCGTCTTGAGTCCAACCCGGTAAGACACGACTTATCGCCACT GGCAGCAGCCACTGGTAACAGGATTAGCAGAGCGAGGTATGT | promoter reporter vector with RenSP |

FIG. 3 (cont.)

| SEQ ID NO | Name | Sequence | Note |
|---|---|---|---|
| | | AGGCGGTGCTACAGAGTTCTTGAAGTGGTGGCCTAACTACGG<br>CTACACTAGAAGAACAGTATTTGGTATCTGCGCTCTGCTGAAG<br>CCAGTTACCTTCGGAAAAAGAGTTGGTAGCTCTTGATCCGGCA<br>AACAAACCACCGCTGGTAGCGGTGGTTTTTTTGTTTGCAAGCA<br>GCAGATTACGCGCAGAAAAAAAGGATCTCAAGAAGATCCTTT<br>GATCTTTTCTACGGGGTCTGACGCTCAGTGGAACGAAAACTCA<br>CGTTAAGGGATTTTGGTCATGAGATTATCAAAAAGGATCTTCA<br>CCTAGATCCTTTTAAATTAAAAATGAAGTTTTAAATCAATCTAA<br>AGTATATATGAGTAAACTTGGTCTGACAGCGGCCGCAAATGCT<br>AAACCACTGCAGTGGTTACCAATGCTTAATCAGTGAGGCACCT<br>ATCTCAGCGATCTGTCTATTTCGTTCATCCATAGTTGCCTGACT<br>CCCCGTCGTGTAGATAACTACGATACGGGAGGGCTTACCATCT<br>GGCCCCAGCGCTGCGATGATACCGCGAGAACCACGCTCACCG<br>GCTCCGGATTTATCAGCAATAAACCAGCCAGCCGGAAGGGCC<br>GAGCGCAGAAGTGGTCCTGCAACTTTATCCGCCTCCATCCAGT<br>CTATTAATTGTTGCCGGGAAGCTAGAGTAAGTAGTTCGCCAGT<br>TAATAGTTTGCGCAACGTTGTTGCCATCGCTACAGGCATCGTG<br>GTGTCACGCTCGTCGTTTGGTATGGCTTCATTCAGCTCCGGTTC<br>CCAACGATCAAGGCGAGTTACATGATCCCCCATGTTGTGCAAA<br>AAAGCGGTTAGCTCCTTCGGTCCTCCGATCGTTGTCAGAAGTA<br>AGTTGGCCGCAGTGTTATCACTCATGGTTATGGCAGCACTGCA<br>TAATTCTCTTACTGTCATGCCATCCGTAAGATGCTTTTCTGTGA<br>CTGGTGAGTACTCAACCAAGTCATTCTGAGAATAGTGTATGCG<br>GCGACCGAGTTGCTCTTGCCCGGCGTCAATACGGGATAATACC<br>GCGCCACATAGCAGAACTTTAAAAGTGCTCATCATTGGAAAAC<br>GTTCTTCGGGGCGAAAACTCTCAAGGATCTTACCGCTGTTGAG<br>ATCCAGTTCGATGTAACCCACTCGTGCACCCAACTGATCTTCAG<br>CATCTTTTACTTTCACCAGCGTTTCTGGGTGAGCAAAAACAGG<br>AAGGCAAAATGCCGCAAAAAAGGGAATAAGGGCGACACGGA<br>AATGTTGAATACTCATACTCGTCCTTTTTCAATATTATTGAAGC<br>ATTTATCAGGGTTACTAGTACGTCTCTCAAGGATAAGTAAGTA<br>ATATTAAGGTACGGGAGGTATTGGACAGGCCGCAATAAAATA<br>TCTTTATTTTCATTACATCTGTGTGTTGGTTTTTTGTGTGAATCG<br>ATAGTACTAACATACGCTCTCCATCAAAACAAAACGAAACAAA<br>ACAAACTAGCAAAATAGGCTGTCCCCAGTGCAAGTGCAGGTG<br>CCAGAACATTTCTCT | |

FIG. 3 (cont.)

| SEQ ID NO | Name | Sequence | Note |
|---|---|---|---|
| SEQ ID NO. 6 | pLightSwitch_3UTR | GGCCTAACTGGCCGGTACCTGAGCTCACGCGTGTACCCGGTCA<br>CCTCTCTGATCTGCGCATGTGCTGGGCTACGCGCGGGCGCAAG<br>CGCCAAGAGCGGCTGCGTCTATGGTCATGACGTCTGACAGAG<br>CGTCCACCCGTCTTCGACAGGACTCTATGGTTCTTACGCGCGC<br>AGACAGACCGCCTATATAAGCCATGCGCAGGCGGAGGAGCGC<br>CTCTTTCCCTTCGGTGTGGGGAGCAAGCGCAGTTGTCGTCTCT<br>TGCGGTGCCGTCGCTGGTTCTCACACCTTTTAGGTCTGTTCTCG<br>TCTTCCCGAGATCTAAGCTTGGCATTCCGGTACTGTTGGTAAA<br>GCCACCATGGCTTCCAAGGTGTACGACCCGGAGCAGCGCAAG<br>AGGATGATCACCGGCCCTCAGTGGTGGGCTCGGTGCAAGCAG<br>ATGAACGTGCTCGACTCCTTCATCAACTACTACGACAGCGAGA<br>AACATGCGGAGAACGCCGTGATCTTCCTCCACGGCAACGCCGC<br>TTCCTCCTACCTGTGGCGCCACGTCGTGCCCCACATCGAGCCC<br>GTCGCCCGGTGCATCATCCCTGATCTGATCGGGATGGGGAAG<br>AGCGGGAAGAGCGGCAACGGCAGCTACCGCCTGCTCGACCAC<br>TACAAGTACCTCACCGCCTGGTTCGAGCTGCTGAACCTCCCCA<br>AGAAGATCATCTTTGTGGGCCACGACTGGGGCGCTTGTCTCGC<br>TTTTCACTACTCCTACGAGCACCAGGATAAGATCAAGGCTATC<br>GTGCATGCTGAGAGCGTCGTGGACGTGATCGAGTCCTGGGAC<br>GAGTGGCCCGATATCGAGGAGGATATTGCTCTGATCAAGTCC<br>GAGGAGGGCGAGAAGATGGTCCTGGAGAATAACTTCTTCGTG<br>GAGACTATGCTGCCTAGCAAGATCATGCGCAAGCTGGAGCCC<br>GAGGAGTTCGCTGCTTACCTGGAGCCCTTCAAGGAGAAGGGC<br>GAGGTCAGAAGACCAACCCTCAGCTGGCCTCGGGAGATCCCT<br>CTGGTCAAGGGCGGGAAGCCGGACGTGGTGCAGATCGTCCG<br>GAACTACAACGCCTACCTGCGCGCCAGCGACGACCTGCCTAAG<br>ATGTTCATCGAGTCCGACCCCGGCTTCTTCAGCAACGCTATCGT<br>GGAGGGCGCCAAGAAGTTCCCCAACACCGAGTTCGTGAAGGT<br>GAAGGGCCTCCACTTCTCCCAAGAGGACGCCCCTGATGAGAT<br>GGGGAAGTACATCAAGAGCTTCGTCGAGCGCGTCCTCAAGAA<br>CGAGCAGAATTCTCACGGCTTCCCTCCCGAGGTGGAGGAGCA<br>GGCCGCCGGCACCCTGCCCATGAGCTGCGCCCAGGAGAGCGG<br>CATGGATAGACACCCTGCTGCTTGCGCCAGCGCCAGGATCAAC<br>GTCTAATCTAGAGCTAGCCCTAGGGATATCCTCGAGGGCCGGC<br>CGCTTCGAGCAGACATGATAAGATACATTGATGAGTTTGGACA<br>AACCACAACTAGAATGCAGTGAAAAAAATGCTTTATTTGTGAA<br>ATTTGTGATGCTATTGCTTTATTTGTAACCATTATAAGCTGCAA<br>TAAACAAGTTAACAACAACAATTGCATTCATTTTATGTTTCAGG<br>TTCAGGGGAGGTGTGGGAGGTTTTTTAAAGCAAGTAAAACC<br>TCTACAAATGTGGTAAAATCGATAAGGATCCGTCGACCGATGC<br>CCTTGAGAGCCTTCAACCCAGTCAGCTCCTTCCGGTGGGCGCG<br>GGGCATGACTATCGTCGCCGCACTTATGACTGTCTTCTTTATCA<br>TGCAACTCGTAGGACAGGTGCCGGCAGCGCTCTTCCGCTTCCT<br>CGCTCACTGACTCGCTGCGCTCGGTCGTTCGGCTGCGGCGAGC<br>GGTATCAGCTCACTCAAAGGCGGTAATACGGTTATCCACAGAA<br>TCAGGGGATAACGCAGGAAAGAACATGTGAGCAAAAGGCCA<br>GCAAAAGGCCAGGAACCGTAAAAAGGCCGCGTTGCTGGCGTT<br>TTTCCATAGGCTCCGCCCCCCTGACGAGCATCACAAAAATCGA<br>CGCTCAAGTCAGAGGTGGCGAAACCCGACAGGACTATAAAGA<br>TACCAGGCGTTTCCCCCTGGAAGCTCCCTCGTGCGCTCTCCTGT | 3'UTR reporter vector with RenSP |

FIG. 3 (cont.)

| SEQ ID NO | Name | Sequence | Note |
|---|---|---|---|

TCCGACCCTGCCGCTTACCGGATACCTGTCCGCCTTTCTCCCTT
CGGGAAGCGTGGCGCTTTCTCATAGCTCACGCTGTAGGTATCT
CAGTTCGGTGTAGGTCGTTCGCTCCAAGCTGGGCTGTGTGCAC
GAACCCCCCGTTCAGCCCGACCGCTGCGCCTTATCCGGTAACT
ATCGTCTTGAGTCCAACCCGGTAAGACACGACTTATCGCCACT
GGCAGCAGCCACTGGTAACAGGATTAGCAGAGCGAGGTATGT
AGGCGGTGCTACAGAGTTCTTGAAGTGGTGGCCTAACTACGG
CTACACTAGAAGAACAGTATTTGGTATCTGCGCTCTGCTGAAG
CCAGTTACCTTCGGAAAAAGAGTTGGTAGCTCTTGATCCGGCA
AACAAACCACCGCTGGTAGCGGTGGTTTTTTTGTTTGCAAGCA
GCAGATTACGCGCAGAAAAAAAGGATCTCAAGAAGATCCTTT
GATCTTTTCTACGGGGTCTGACGCTCAGTGGAACGAAAACTCA
CGTTAAGGGATTTTGGTCATGAGATTATCAAAAAGGATCTTCA
CCTAGATCCTTTTAAATTAAAAATGAAGTTTTAAATCAATCTAA
AGTATATATGAGTAAACTTGGTCTGACAGCGGCCGCAAATGCT
AAACCACTGCAGTGGTTACCAATGCTTAATCAGTGAGGCACCT
ATCTCAGCGATCTGTCTATTTCGTTCATCCATAGTTGCCTGACT
CCCCGTCGTGTAGATAACTACGATACGGGAGGGCTTACCATCT
GGCCCCAGCGCTGCGATGATACCGCGAGAACCACGCTCACCG
GCTCCGGATTTATCAGCAATAAACCAGCCAGCCGGAAGGGCC
GAGCGCAGAAGTGGTCCTGCAACTTTATCCGCCTCCATCCAGT
CTATTAATTGTTGCCGGGAAGCTAGAGTAAGTAGTTCGCCAGT
TAATAGTTTGCGCAACGTTGTTGCCATCGCTACAGGCATCGTG
GTGTCACGCTCGTCGTTTGGTATGGCTTCATTCAGCTCCGGTTC
CCAACGATCAAGGCGAGTTACATGATCCCCCATGTTGTGCAAA
AAAGCGGTTAGCTCCTTCGGTCCTCCGATCGTTGTCAGAAGTA
AGTTGGCCGCAGTGTTATCACTCATGGTTATGGCAGCACTGCA
TAATTCTCTTACTGTCATGCCATCCGTAAGATGCTTTTCTGTGA
CTGGTGAGTACTCAACCAAGTCATTCTGAGAATAGTGTATGCG
GCGACCGAGTTGCTCTTGCCCGGCGTCAATACGGGATAATACC
GCGCCACATAGCAGAACTTTAAAAGTGCTCATCATTGGAAAAC
GTTCTTCGGGGCGAAAACTCTCAAGGATCTTACCGCTGTTGAG
ATCCAGTTCGATGTAACCCACTCGTGCACCCAACTGATCTTCAG
CATCTTTTACTTTCACCAGCGTTTCTGGGTGAGCAAAAACAGG
AAGGCAAAATGCCGCAAAAAAGGGAATAAGGGCGACACGGA
AATGTTGAATACTCATACTCGTCCTTTTTCAATATTATTGAAGC
ATTTATCAGGGTTACTAGTACGTCTCTCAAGGATAAGTAAGTA
ATATTAAGGTACGGGAGGTATTGGACAGGCCGCAATAAAATA
TCTTTATTTTCATTACATCTGTGTGTTGGTTTTTTGTGTGAATCG
ATAGTACTAACATACGCTCTCCATCAAAACAAAACGAAACAAA
ACAAACTAGCAAAATAGGCTGTCCCCAGTGCAAGTGCAGGTG
CCAGAACATTTCTCT

FIG. 3 (cont.)

| SEQ ID NO | Name | Sequence | Note |
|---|---|---|---|
| SEQ ID NO. 7 | pLightSwitch_LR | GGCCTAACTGGCCGGTACCTGAGCTCTTACGCGTGCTAGCCCG GGCTCGAGATCTGCGATCTAAGTAAGCTTCGTTTGCTGGCGGT GTCCCCGGAAGAAATATATTTGCATGTCTTTAGTTCTATGATGA CACAAACCCCGCCCAGCGTCTTGTCATTGGCGAATTCGAACAC GCAGATGCAGTCGGGGCGGCGCGGTCCCAGGTCCACTTCGCA TATTAAGGTGACGCGCGTGGCCTCGAACACCGAGCGACCCTG CAGCGACCCGCTTAAGGCAATCCGGTACTGTTGGTAAAGCCAC CATGGCTTCCAAGGTGTACGACCCGGAGCAGCGCAAGAGGAT GATCACCGGCCCTCAGTGGTGGGCTCGGTGCAAGCAGATGAA CGTGCTCGACTCCTTCATCAACTACTACGACAGCGAGAAACAT GCGGAGAACGCCGTGATCTTCCTCCACGGCAACGCCGCTTCCT CCTACCTGTGGCGCCACGTCGTGCCCCACATCGAGCCCGTCGC CCGGTGCATCATCCCTGATCTGATCGGGATGGGGAAGAGCGG GAAGAGCGGCAACGGCAGCTACCGCCTGCTCGACCACTACAA GTACCTCACCGCCTGGTTCGAGCTGCTGAACCTCCCCAAGAAG ATCATCTTTGTGGGCCACGACTGGGGCGCTTGTCTCGCTTTTCA CTACTCCTACGAGCACCAGGATAAGATCAAGGCTATCGTGCAT GCTGAGAGCGTCGTGGACGTGATCGAGTCCTGGGACGAGTGG CCCGATATCGAGGAGGATATTGCTCTGATCAAGTCCGAGGAG GGCGAGAAGATGGTCCTGGAGAATAACTTCTTCGTGGAGACT ATGCTGCCTAGCAAGATCATGCGCAAGCTGGAGCCCGAGGAG TTCGCTGCTTACCTGGAGCCCTTCAAGGAGAAGGGCGAGGTC AGAAGACCAACCCTCAGCTGGCCTCGGGAGATCCCTCTGGTCA AGGGCGGGAAGCCGGACGTGGTGCAGATCGTCCGGAACTAC AACGCCTACCTGCGCGCCAGCGACGACCTGCCTAAGATGTTCA TCGAGTCCGACCCCGGCTTCTTCAGCAACGCTATCGTGGAGGG CGCCAAGAAGTTCCCCAACACCGAGTTCGTGAAGGTGAAGGG CCTCCACTTCTCCCAAGAGGACGCCCCTGATGAGATGGGGAA GTACATCAAGAGCTTCGTCGAGCGCGTCCTCAAGAACGAGCA GAATTCTCACGGCTTCCCTCCCGAGGTGGAGGAGCAGGCCGC CGGCACCCTGCCCATGAGCTGCGCCCAGGAGAGCGGCATGGA TAGACACCCTGCTGCTTGCGCCAGCGCCAGGATCAACGTCTAA TCTAGAGTCGGGGCGGCCGGCCGCTTCGAGCAGACATGATAA GATACATTGATGAGTTTGGACAAACCACAACTAGAATGCAGTG AAAAAAATGCTTTATTTGTGAAATTTGTGATGCTATTGCTTTAT TTGTAACCATTATAAGCTGCAATAAACAAGTTAACAACAACAA TTGCATTCATTTTATGTTTCAGGTTCAGGGGGAGGTGTGGGAG GTTTTTTAAAGCAAGTAAAACCTCTACAAATGTGGTAAAATCG ATAAGGATCCGTCGACCGATGCCCTTGAGAGCCTTCAACCCAG TCAGCTCCTTCCGGTGGGCGCGGGGCATGACTATCGTCGCCGC ACTTATGACTGTCTTCTTTATCATGCAACTCGTAGGACAGGTGC CGGCAGCGCTCTTCCGCTTCCTCGCTCACTGACTCGCTGCGCTC GGTCGTTCGGCTGCGGCGAGCGGTATCAGCTCACTCAAAGGC GGTAATACGGTTATCCACAGAATCAGGGGATAACGCAGGAAA GAACATGTGAGCAAAAGGCCAGCAAAAGGCCAGGAACCGTA AAAAGGCCGCGTTGCTGGCGTTTTTCCATAGGCTCCGCCCCCC TGACGAGCATCACAAAAATCGACGCTCAAGTCAGAGGTGGCG AAACCCGACAGGACTATAAAGATACCAGGCGTTTCCCCCTGGA AGCTCCCTCGTGCGCTCTCCTGTTCCGACCCTGCCGCTTACCGG ATACCTGTCCGCCTTTCTCCCTTCGGGAAGCGTGGCGCTTTCTC | long-range element reporter vector with RenSP |

FIG. 3 (cont.)

| SEQ ID NO | Name | Sequence | Note |
|---|---|---|---|
| | | ATAGCTCACGCTGTAGGTATCTCAGTTCGGTGTAGGTCGTTCG | |
| | | CTCCAAGCTGGGCTGTGTGCACGAACCCCCCGTTCAGCCCGAC | |
| | | CGCTGCGCCTTATCCGGTAACTATCGTCTTGAGTCCAACCCGGT | |
| | | AAGACACGACTTATCGCCACTGGCAGCAGCCACTGGTAACAG | |
| | | GATTAGCAGAGCGAGGTATGTAGGCGGTGCTACAGAGTTCTT | |
| | | GAAGTGGTGGCCTAACTACGGCTACACTAGAAGAACAGTATTT | |
| | | GGTATCTGCGCTCTGCTGAAGCCAGTTACCTTCGGAAAAAGAG | |
| | | TTGGTAGCTCTTGATCCGGCAAACAAACCACCGCTGGTAGCGG | |
| | | TGGTTTTTTTGTTTGCAAGCAGCAGATTACGCGCAGAAAAAAA | |
| | | GGATCTCAAGAAGATCCTTTGATCTTTTCTACGGGGTCTGACG | |
| | | CTCAGTGGAACGAAAACTCACGTTAAGGGATTTTGGTCATGAG | |
| | | ATTATCAAAAAGGATCTTCACCTAGATCCTTTTAAATTAAAAAT | |
| | | GAAGTTTTAAATCAATCTAAAGTATATATGAGTAAACTTGGTCT | |
| | | GACAGCGGCCGCAAATGCTAAACCACTGCAGTGGTTACCAAT | |
| | | GCTTAATCAGTGAGGCACCTATCTCAGCGATCTGTCTATTTCGT | |
| | | TCATCCATAGTTGCCTGACTCCCCGTCGTGTAGATAACTACGAT | |
| | | ACGGGAGGGCTTACCATCTGGCCCCAGCGCTGCGATGATACC | |
| | | GCGAGAACCACGCTCACCGGCTCCGGATTTATCAGCAATAAAC | |
| | | CAGCCAGCCGGAAGGGCCGAGCGCAGAAGTGGTCCTGCAACT | |
| | | TTATCCGCCTCCATCCAGTCTATTAATTGTTGCCGGGAAGCTAG | |
| | | AGTAAGTAGTTCGCCAGTTAATAGTTTGCGCAACGTTGTTGCC | |
| | | ATCGCTACAGGCATCGTGGTGTCACGCTCGTCGTTTGGTATGG | |
| | | CTTCATTCAGCTCCGGTTCCCAACGATCAAGGCGAGTTACATG | |
| | | ATCCCCCATGTTGTGCAAAAAAGCGGTTAGCTCCTTCGGTCCTC | |
| | | CGATCGTTGTCAGAAGTAAGTTGGCCGCAGTGTTATCACTCAT | |
| | | GGTTATGGCAGCACTGCATAATTCTCTTACTGTCATGCCATCCG | |
| | | TAAGATGCTTTTCTGTGACTGGTGAGTACTCAACCAAGTCATTC | |
| | | TGAGAATAGTGTATGCGGCGACCGAGTTGCTCTTGCCCGGCGT | |
| | | CAATACGGGATAATACCGCGCCACATAGCAGAACTTTAAAAGT | |
| | | GCTCATCATTGGAAAACGTTCTTCGGGGCGAAAACTCTCAAGG | |
| | | ATCTTACCGCTGTTGAGATCCAGTTCGATGTAACCCACTCGTGC | |
| | | ACCCAACTGATCTTCAGCATCTTTTACTTTCACCAGCGTTTCTG | |
| | | GGTGAGCAAAAACAGGAAGGCAAAATGCCGCAAAAAAGGGA | |
| | | ATAAGGGCGACACGGAAATGTTGAATACTCATACTCGTCCTTT | |
| | | TTCAATATTATTGAAGCATTTATCAGGGTTACTAGTACGTCTCT | |
| | | CAAGGATAAGTAAGTAATATTAAGGTACGGGAGGTATTGGAC | |
| | | AGGCCGCAATAAAATATCTTTATTTTCATTACATCTGTGTGTTG | |
| | | GTTTTTTGTGTGAATCGATAGTACTAACATACGCTCTCCATCAA | |
| | | AACAAAACGAAACAAAACAAACTAGCAAAATAGGCTGTCCCC | |
| | | AGTGCAAGTGCAGGTGCCAGAACATTTCTCT | |

FIG. 3 (cont.)

| SEQ ID NO | Name | Sequence | Note |
|---|---|---|---|
| SEQ ID NO. 8 | pLightSwitch_5UTR | GGCCTAACTGGCCGGTACCTGAGCTCTTACGCGTATAGCAGAC<br>ATACAACGGACGGTGGGCCCAGACCCAGGCTGTGTAGACCCA<br>GCCCCCCCGCCCCGCAGTGCCTAGGTCACCCACTAACGCCCCA<br>GGCCTTGTCTTGGCTGGGCGTGACTGTTACCCTCAAAAGCAGG<br>CAGCTCCAGGGTAAAAGGTGCCCTGCCCTGTAGAGCCCACCTT<br>CCTTCCCAGGGCTGCGGCTGGGTAGGTTTGTAGCCTTCATCAC<br>GGGCCACCTCCAGCCACTGGACCGCTGGCCCCTGCCCTGTCCT<br>GGGGAGTGTGGTCCTGCGACTTCTAAGTGGCCGCAAGCCACC<br>TGACTCCCCCAACACCACACTCTACCTCTCAAGCCCAGGTCTCT<br>CCCTAGTGACCCACCCAGCACATTTAGCTAGCTGAGCCCCACA<br>GCCAGAGGTCCTCAGGCCCTGCTTTCAGGGCAGTTGCTCTGAA<br>GTCGGCAAGGGGGAGTGACTGCCTGGCCACTCCATGCCCTCC<br>AAGAGCTCCTTCTGCAGGAGCGTACAGAACCCAGGGCCCTGG<br>CACCCGTGCAGACCCTGGCCCACCCCACCTGGGCGCTCAGTGC<br>CAAGAGATGTCCACACCTAGGATGTCCCGCGGTGGGTGGGG<br>GGCCCGAGAGACGGGCAGGCCGGGGGCAGGCCTGGCCATGC<br>GGGGCCGAACCGGGCACTGCCCAGCGTGGGGCGCGGGGGCC<br>ACGGCGCGCGCCCCAGCCCCGGGCCCAGCACCCCAAGGCG<br>GCCAACGCCAAAACTCTCCCTCCTCCTCTTCCTCAATCTCGCTCT<br>CGCTCTTTTTTTTTTTCGCAAAAGGAGGGGAGAGGGGGTAAAA<br>AAATGCTGCACTGTGCGGCGAAGCCGGTGAGTGAGCGGCGC<br>GGGGCCAATCAGCGTGCGCCGTTCCGAAAGTTGCCTTTTATGG<br>CTCGAGCGGCCGCGGCGGCGCCCTATAAAACCCAGCGGCGCG<br>ACGCGCCACCACCGCCGAGACCGCGTCCGCCCCGAGATCTCA<br>GAGCCTCGCCTTTCTTAAGCCGATCCGCCGGACGTCCACACCC<br>CCTGCAGGCTCACCCATGGCTTCCAAGGTGTACGACCCGGAGC<br>AGCGCAAGAGGATGATCACCGGCCCTCAGTGGTGGGCTCGGT<br>GCAAGCAGATGAACGTGCTCGACTCCTTCATCAACTACTACGA<br>CAGCGAGAAACATGCGGAGAACGCCGTGATCTTCCTCCACGG<br>CAACGCCGCTTCCTCCTACCTGTGGCGCCACGTCGTGCCCCAC<br>ATCGAGCCCGTCGCCCGGTGCATCATCCCTGATCTGATCGGGA<br>TGGGGAAGAGCGGGAAGAGCGGCAACGGCAGCTACCGCCTG<br>CTCGACCACTACAAGTACCTCACCGCCTGGTTCGAGCTGCTGA<br>ACCTCCCCAAGAAGATCATCTTTGTGGGCCACGACTGGGGCGC<br>TTGTCTCGCTTTTCACTACTCCTACGAGCACCAGGATAAGATCA<br>AGGCTATCGTGCATGCTGAGAGCGTCGTGGACGTGATCGAGT<br>CCTGGGACGAGTGGCCCGATATCGAGGAGGATATTGCTCTGA<br>TCAAGTCCGAGGAGGGCGAGAAGATGGTCCTGGAGAATAACT<br>TCTTCGTGGAGACTATGCTGCCTAGCAAGATCATGCGCAAGCT<br>GGAGCCCGAGGAGTTCGCTGCTTACCTGGAGCCCTTCAAGGA<br>GAAGGGCGAGGTCAGAAGACCAACCCTCAGCTGGCCTCGGGA<br>GATCCCTCTGGTCAAGGGCGGGAAGCCGGACGTGGTGCAGAT<br>CGTCCGGAACTACAACGCCTACCTGCGCGCCAGCGACGACCTG<br>CCTAAGATGTTCATCGAGTCCGACCCCGGCTTCTTCAGCAACG<br>CTATCGTGGAGGGCGCCAAGAAGTTCCCCAACACCGAGTTCGT<br>GAAGGTGAAGGGCCTCCACTTCTCCCAAGAGGACGCCCCTGA<br>TGAGATGGGGAAGTACATCAAGAGCTTCGTCGAGCGCGTCCT<br>CAAGAACGAGCAGAATTCTCACGGCTTCCCTCCCGAGGTGGA<br>GGAGCAGGCCGCCGGCACCCTGCCCATGAGCTGCGCCCAGGA<br>GAGCGGCATGGATAGACACCCTGCTGCTTGCGCCAGCGCCAG | 5'UTR reporter vector with RenSP |

FIG. 3 (cont.)

| SEQ ID NO | Name | Sequence | Note |
|---|---|---|---|
| | | GATCAACGTCTAATCTAGAGTCGGGGCGGCCGGCCGCTTCGA | |
| | | GCAGACATGATAAGATACATTGATGAGTTTGGACAAACCACAA | |
| | | CTAGAATGCAGTGAAAAAAATGCTTTATTTGTGAAATTTGTGA | |
| | | TGCTATTGCTTTATTTGTAACCATTATAAGCTGCAATAAACAAG | |
| | | TTAACAACAACAATTGCATTCATTTTATGTTTCAGGTTCAGGGG | |
| | | GAGGTGTGGGAGGTTTTTTAAAGCAAGTAAAACCTCTACAAAT | |
| | | GTGGTAAAATCGATAAGGATCCGTCGACCGATGCCCTTGAGA | |
| | | GCCTTCAACCCAGTCAGCTCCTTCCGGTGGGCGCGGGGCATGA | |
| | | CTATCGTCGCCGCACTTATGACTGTCTTCTTTATCATGCAACTC | |
| | | GTAGGACAGGTGCCGGCAGCGCTCTTCCGCTTCCTCGCTCACT | |
| | | GACTCGCTGCGCTCGGTCGTTCGGCTGCGGCGAGCGGTATCA | |
| | | GCTCACTCAAAGGCGGTAATACGGTTATCCACAGAATCAGGG | |
| | | GATAACGCAGGAAAGAACATGTGAGCAAAAGGCCAGCAAAA | |
| | | GGCCAGGAACCGTAAAAAGGCCGCGTTGCTGGCGTTTTTCCAT | |
| | | AGGCTCCGCCCCCCTGACGAGCATCACAAAAATCGACGCTCAA | |
| | | GTCAGAGGTGGCGAAACCCGACAGGACTATAAAGATACCAGG | |
| | | CGTTTCCCCCTGGAAGCTCCCTCGTGCGCTCTCCTGTTCCGACC | |
| | | CTGCCGCTTACCGGATACCTGTCCGCCTTTCTCCCTTCGGGAAG | |
| | | CGTGGCGCTTTCTCATAGCTCACGCTGTAGGTATCTCAGTTCG | |
| | | GTGTAGGTCGTTCGCTCCAAGCTGGGCTGTGTGCACGAACCCC | |
| | | CCGTTCAGCCCGACCGCTGCGCCTTATCCGGTAACTATCGTCTT | |
| | | GAGTCCAACCCGGTAAGACACGACTTATCGCCACTGGCAGCA | |
| | | GCCACTGGTAACAGGATTAGCAGAGCGAGGTATGTAGGCGGT | |
| | | GCTACAGAGTTCTTGAAGTGGTGGCCTAACTACGGCTACACTA | |
| | | GAAGAACAGTATTTGGTATCTGCGCTCTGCTGAAGCCAGTTAC | |
| | | CTTCGGAAAAAGAGTTGGTAGCTCTTGATCCGGCAAACAAACC | |
| | | ACCGCTGGTAGCGGTGGTTTTTTTGTTTGCAAGCAGCAGATTA | |
| | | CGCGCAGAAAAAAAGGATCTCAAGAAGATCCTTTGATCTTTTC | |
| | | TACGGGGTCTGACGCTCAGTGGAACGAAAACTCACGTTAAGG | |
| | | GATTTTGGTCATGAGATTATCAAAAAGGATCTTCACCTAGATC | |
| | | CTTTTAAATTAAAAATGAAGTTTTAAATCAATCTAAAGTATATA | |
| | | TGAGTAAACTTGGTCTGACAGCGGCCGCAAATGCTAAACCACT | |
| | | GCAGTGGTTACCAATGCTTAATCAGTGAGGCACCTATCTCAGC | |
| | | GATCTGTCTATTTCGTTCATCCATAGTTGCCTGACTCCCCGTCG | |
| | | TGTAGATAACTACGATACGGGAGGGCTTACCATCTGGCCCCAG | |
| | | CGCTGCGATGATACCGCGAGAACCACGCTCACCGGCTCCGGA | |
| | | TTTATCAGCAATAAACCAGCCAGCCGGAAGGGCCGAGCGCAG | |
| | | AAGTGGTCCTGCAACTTTATCCGCCTCCATCCAGTCTATTAATT | |
| | | GTTGCCGGGAAGCTAGAGTAAGTAGTTCGCCAGTTAATAGTTT | |
| | | GCGCAACGTTGTTGCCATCGCTACAGGCATCGTGGTGTCACGC | |
| | | TCGTCGTTTGGTATGGCTTCATTCAGCTCCGGTTCCCAACGATC | |
| | | AAGGCGAGTTACATGATCCCCCATGTTGTGCAAAAAAGCGGTT | |
| | | AGCTCCTTCGGTCCTCCGATCGTTGTCAGAAGTAAGTTGGCCG | |
| | | CAGTGTTATCACTCATGGTTATGGCAGCACTGCATAATTCTCTT | |
| | | ACTGTCATGCCATCCGTAAGATGCTTTTCTGTGACTGGTGAGT | |
| | | ACTCAACCAAGTCATTCTGAGAATAGTGTATGCGGCGACCGAG | |
| | | TTGCTCTTGCCCGGCGTCAATACGGGATAATACCGCGCCACAT | |
| | | AGCAGAACTTTAAAAGTGCTCATCATTGGAAAACGTTCTTCGG | |
| | | GGCGAAAACTCTCAAGGATCTTACCGCTGTTGAGATCCAGTTC | |
| | | GATGTAACCCACTCGTGCACCCAACTGATCTTCAGCATCTTTTA | |

| SEQ ID NO | Name | Sequence | Note |
|---|---|---|---|
| | | CTTTCACCAGCGTTTCTGGGTGAGCAAAAACAGGAAGGCAAA<br>ATGCCGCAAAAAAGGGAATAAGGGCGACACGGAAATGTTGA<br>ATACTCATACTCGTCCTTTTTCAATATTATTGAAGCATTTATCAG<br>GGTTACTAGTACGTCTCTCAAGGATAAGTAAGTAATATTAAGG<br>TACGGGAGGTATTGGACAGGCCGCAATAAAATATCTTTATTTT<br>CATTACATCTGTGTGTTGGTTTTTTGTGTGAATCGATAGTACTA<br>ACATACGCTCTCCATCAAAACAAAACGAAACAAAACAAACTAG<br>CAAAATAGGCTGTCCCCAGTGCAAGTGCAGGTGCCAGAACAT<br>TTCTCT | |
| SEQ ID NO. 9 | AFP1 | GTGYARTTAAT | transcription factor recognition motif excluded from RenSP sequence |
| SEQ ID NO. 10 | AHR | GCGTG | transcription factor recognition motif excluded from RenSP sequence |
| SEQ ID NO. 11 | ALPHA-CP1 | CAGCCAATGAG | transcription factor recognition motif excluded from RenSP sequence |
| SEQ ID NO. 12 | AMEF-2 | KKRGTTATTTTTARNCMG | transcription factor recognition motif excluded from RenSP sequence |

FIG. 3 (cont.)

| SEQ ID NO | Name | Sequence | Note |
|---|---|---|---|
| SEQ ID NO. 13 | AML1 | ACCACA | transcription factor recognition motif excluded from RenSP sequence |
| SEQ ID NO. 14 | AP-1 | CTGASTCA | transcription factor recognition motif excluded from RenSP sequence |
| SEQ ID NO. 15 | AP-2ALPHA | SCYNNGGC | transcription factor recognition motif excluded from RenSP sequence |
| SEQ ID NO. 16 | AP-4 | GCAGCTGNY | transcription factor recognition motif excluded from RenSP sequence |
| SEQ ID NO. 17 | AREB6 | WCAGGTGWNW | transcription factor recognition motif excluded from RenSP sequence |
| SEQ ID NO. 18 | AREB6 | ANWCAGGTRNR | transcription factor recognition motif excluded from RenSP sequence |
| SEQ ID NO. 19 | ATF-1 | TGACGTCARRG | transcription factor recognition motif excluded from RenSP sequence |
| SEQ ID NO. 20 | ATF6 | TGACGTGG | transcription factor recognition motif excluded from RenSP sequence |
| SEQ ID NO. 21 | BACH2 | SRTGAGTCANC | transcription factor recognition motif excluded from RenSP sequence |
| SEQ ID NO. 22 | BRN-2 | YKNATTWYSNATG | transcription factor recognition motif excluded from RenSP sequence |
| SEQ ID NO. 23 | C/EBPBETA | KNTTGCNYAAY | transcription factor recognition motif excluded from RenSP sequence |
| SEQ ID NO. 24 | CAC-BP | GRGGSTGGG | transcription factor recognition motif excluded from RenSP sequence |
| SEQ ID NO. 25 | CDC5 | GATTTAACATAA | transcription factor recognition motif |

FIG. 3 (cont.)

| SEQ ID NO | Name | Sequence | Note |
|---|---|---|---|
| SEQ ID NO. 26 | CDP | RNTAATCGATNW | transcription factor recognition motif excluded from RenSP sequence |
| SEQ ID NO. 27 | CDX-2 | GGYMATAAAANTNT | transcription factor recognition motif excluded from RenSP sequence |
| SEQ ID NO. 28 | CHOP-C/EBPALPHA | RTGCAATMCCC | transcription factor recognition motif excluded from RenSP sequence |
| SEQ ID NO. 29 | CHX10 | GCTAATTA | transcription factor recognition motif excluded from RenSP sequence |
| SEQ ID NO. 30 | CP2/LBP-1C/LSF | GCTGGNTNGNNCYNG | transcription factor recognition motif excluded from RenSP sequence |
| SEQ ID NO. 31 | CR1 | SCGATCGAT | transcription factor recognition motif excluded from RenSP sequence |
| SEQ ID NO. 32 | CREB | TGACG | transcription factor recognition motif excluded from RenSP sequence |
| SEQ ID NO. 33 | C-REL | GGNNTTYCC | transcription factor recognition motif excluded from RenSP sequence |
| SEQ ID NO. 34 | CRX | KGRGATTANNNR | transcription factor recognition motif excluded from RenSP sequence |
| SEQ ID NO. 35 | DBP | GTNTGCT | transcription factor recognition motif excluded from RenSP sequence |
| SEQ ID NO. 36 | E2F | GCGCSAAA | transcription factor recognition motif excluded from RenSP sequence |
| SEQ ID NO. 37 | E4BP4 | RTTACRTAAY | transcription factor recognition motif excluded from RenSP sequence |

FIG. 3 (cont.)

| SEQ ID NO | Name | Sequence | Note |
|---|---|---|---|
| SEQ ID NO. 38 | E4F1 | GTGACGTARS | transcription factor recognition motif excluded from RenSP sequence |
| SEQ ID NO. 39 | EGR | GTGGGSGCRRS | transcription factor recognition motif excluded from RenSP sequence |
| SEQ ID NO. 40 | ELF-1 | RNWMNAGGAART | transcription factor recognition motif excluded from RenSP sequence |
| SEQ ID NO. 41 | ELK-1 | CCGGAART | transcription factor recognition motif excluded from RenSP sequence |
| SEQ ID NO. 42 | ER | RNNNTGACCT | transcription factor recognition motif excluded from RenSP sequence |
| SEQ ID NO. 43 | ETS | CACTTCCTG | transcription factor recognition motif excluded from RenSP sequence |
| SEQ ID NO. 44 | FAC1 | TNYGTGTTKTG | transcription factor recognition motif excluded from RenSP sequence |
| SEQ ID NO. 45 | FOX | WAAAYAAACAATM | transcription factor recognition motif excluded from RenSP sequence |
| SEQ ID NO. 46 | FOXO1 | RWAAACAA | transcription factor recognition motif excluded from RenSP sequence |
| SEQ ID NO. 47 | FREAC-3 | TGTTTATTTAC | transcription factor recognition motif excluded from RenSP sequence |
| SEQ ID NO. 48 | FREAC-4 | CTWAWGTAAACANWG | transcription factor recognition motif excluded from RenSP sequence |
| SEQ ID NO. 49 | GABP | CGGAAG | transcription factor recognition motif excluded from RenSP sequence |
| SEQ ID NO. 50 | GATA | WGATAR | transcription factor recognition motif |

FIG. 3 (cont.)

| SEQ ID NO | Name | Sequence | Note |
|---|---|---|---|
| SEQ ID NO. 51 | HIF-1 | CCGCACGT | excluded from RenSP sequence transcription factor recognition motif |
| SEQ ID NO. 52 | HNF-1 | GGTTAATNWTTAMC | excluded from RenSP sequence transcription factor recognition motif |
| SEQ ID NO. 53 | HNF-3 | TRTTTRYTYW | excluded from RenSP sequence transcription factor recognition motif |
| SEQ ID NO. 54 | HNF-4 | TGAMCTTTGMMCYT | excluded from RenSP sequence transcription factor recognition motif |
| SEQ ID NO. 55 | HNF-6 | NWAAATCAATAW | excluded from RenSP sequence transcription factor recognition motif |
| SEQ ID NO. 56 | HOXA4 | CYAATTWT | excluded from RenSP sequence transcription factor recognition motif |
| SEQ ID NO. 57 | HP1 | CTGTTGAAWATT | excluded from RenSP sequence transcription factor recognition motif |
| SEQ ID NO. 58 | HSF2 | GAANNTTC | excluded from RenSP sequence transcription factor recognition motif |
| SEQ ID NO. 59 | ICSBP | CAGTTTCAYTTY | excluded from RenSP sequence transcription factor recognition motif |
| SEQ ID NO. 60 | IK-1 | GGYATTCCCANN | excluded from RenSP sequence transcription factor recognition motif |
| SEQ ID NO. 61 | IPF1 | KGTCATTANNNC | excluded from RenSP sequence transcription factor recognition motif |
| SEQ ID NO. 62 | IRF | NNCRSTTTCANTTYY | excluded from RenSP sequence transcription factor recognition motif |

FIG. 3 (cont.)

| SEQ ID NO | Name | Sequence | Note |
|---|---|---|---|
| SEQ ID NO. 63 | IRF1 | AAGTGAA | transcription factor recognition motif excluded from RenSP sequence |
| SEQ ID NO. 64 | IRF-1 | GGTTTCRCTTTTS | transcription factor recognition motif excluded from RenSP sequence |
| SEQ ID NO. 65 | IRF-7 | ANTTTCGNWTTCSNA | transcription factor recognition motif excluded from RenSP sequence |
| SEQ ID NO. 66 | IY | AWTTTCC | transcription factor recognition motif excluded from RenSP sequence |
| SEQ ID NO. 67 | LEF1 | CTTTGA | transcription factor recognition motif excluded from RenSP sequence |
| SEQ ID NO. 68 | LHX3 | TTAATTAATT | transcription factor recognition motif excluded from RenSP sequence |
| SEQ ID NO. 69 | LYF-1 | YCTCCCAAA | transcription factor recognition motif excluded from RenSP sequence |
| SEQ ID NO. 70 | MAZ | GGGGAGGG | transcription factor recognition motif excluded from RenSP sequence |
| SEQ ID NO. 71 | MEF-2 | YTAAAWATAGCY | transcription factor recognition motif excluded from RenSP sequence |
| SEQ ID NO. 72 | MEIS1 | TGACAG | transcription factor recognition motif excluded from RenSP sequence |
| SEQ ID NO. 73 | MIF-1 | GTTGCWWGGYAACNGS | transcription factor recognition motif excluded from RenSP sequence |
| SEQ ID NO. 74 | MTF-1 | TNTGCACNCGGCCC | transcription factor recognition motif excluded from RenSP sequence |
| SEQ ID NO. 75 | MYB | GNCNGTT | transcription factor recognition motif |

FIG. 3 (cont.)

| SEQ ID NO | Name | Sequence | Note |
|---|---|---|---|
| SEQ ID NO. 76 | MYC | CACGTG | transcription factor recognition motif excluded from RenSP sequence |
| SEQ ID NO. 77 | MYOD | RNCAGGTG | transcription factor recognition motif excluded from RenSP sequence |
| SEQ ID NO. 78 | NCX | GTAAKTNG | transcription factor recognition motif excluded from RenSP sequence |
| SEQ ID NO. 79 | NF-1 | TGGNNNNNNGCCAA | transcription factor recognition motif excluded from RenSP sequence |
| SEQ ID NO. 80 | NF-AT | TGGAAA | transcription factor recognition motif excluded from RenSP sequence |
| SEQ ID NO. 81 | NF-E2 | RTGACTCAGCA | transcription factor recognition motif excluded from RenSP sequence |
| SEQ ID NO. 82 | NF-MUE1 | CGGCCATCT | transcription factor recognition motif excluded from RenSP sequence |
| SEQ ID NO. 83 | NF-Y | YSATTGGYY | transcription factor recognition motif excluded from RenSP sequence |
| SEQ ID NO. 84 | NKX2-5 | CWTAATTG | transcription factor recognition motif excluded from RenSP sequence |
| SEQ ID NO. 85 | NKX2-5 | TYAAGTG | transcription factor recognition motif excluded from RenSP sequence |
| SEQ ID NO. 86 | NKX6-1 | TWTTTAATTGGTT | transcription factor recognition motif excluded from RenSP sequence |
| SEQ ID NO. 87 | NKX6-2 | WANTAAWTA | transcription factor recognition motif excluded from RenSP sequence |

FIG. 3 (cont.)

| SEQ ID NO | Name | Sequence | Note |
|---|---|---|---|
| SEQ ID NO. 88 | NRF-1 | YGCGCATGCG | transcription factor recognition motif excluded from RenSP sequence |
| SEQ ID NO. 89 | NRSF | TTCAGCACCACGGACAGMGCC | transcription factor recognition motif excluded from RenSP sequence |
| SEQ ID NO. 90 | OCTAMER | ATGCAAATNA | transcription factor recognition motif excluded from RenSP sequence |
| SEQ ID NO. 91 | OLF-1 | CMNNYTCYCTRGGGANTNG | transcription factor recognition motif excluded from RenSP sequence |
| SEQ ID NO. 92 | P300 | GGGAGTNNNNS | transcription factor recognition motif excluded from RenSP sequence |
| SEQ ID NO. 93 | P65 | GGGRATTTCC | transcription factor recognition motif excluded from RenSP sequence |
| SEQ ID NO. 94 | PAX | GTKAGTTCCAG | transcription factor recognition motif excluded from RenSP sequence |
| SEQ ID NO. 95 | PAX-4 | AAWAATTANS | transcription factor recognition motif excluded from RenSP sequence |
| SEQ ID NO. 96 | PBX-1 | WTGATTGNT | transcription factor recognition motif excluded from RenSP sequence |
| SEQ ID NO. 97 | PEA3 | MGGAWGT | transcription factor recognition motif excluded from RenSP sequence |
| SEQ ID NO. 98 | PITX2 | YTGGGATTANW | transcription factor recognition motif excluded from RenSP sequence |
| SEQ ID NO. 99 | POU1F1 | ATGAATAAWT | transcription factor recognition motif excluded from RenSP sequence |
| SEQ ID NO. 100 | POU3F2 | ATTARCATAA | transcription factor recognition motif |

FIG. 3 (cont.)

| SEQ ID NO | Name | Sequence | Note |
|---|---|---|---|
| SEQ ID NO. 101 | POU6F1 | GCATAAWTTAT | transcription factor recognition motif excluded from RenSP sequence |
| SEQ ID NO. 102 | PTF1-BETA | SCTGWNNKTTTCYC | transcription factor recognition motif excluded from RenSP sequence |
| SEQ ID NO. 103 | PU.1 | WGAGGAAG | transcription factor recognition motif excluded from RenSP sequence |
| SEQ ID NO. 104 | RFX1 | GTTRCYWNGYNAC | transcription factor recognition motif excluded from RenSP sequence |
| SEQ ID NO. 105 | RORALPHA2 | TGACCTANWTW | transcription factor recognition motif excluded from RenSP sequence |
| SEQ ID NO. 106 | RP58 | TCCAGATGTT | transcription factor recognition motif excluded from RenSP sequence |
| SEQ ID NO. 107 | RREB-1 | GGGGKKGTTTGGGG | transcription factor recognition motif excluded from RenSP sequence |
| SEQ ID NO. 108 | SF-1 | TGRCCTTG | transcription factor recognition motif excluded from RenSP sequence |
| SEQ ID NO. 109 | SMAD-3 | TGTCTGTCT | transcription factor recognition motif excluded from RenSP sequence |
| SEQ ID NO. 110 | SOX-5 | ATTGTT | transcription factor recognition motif excluded from RenSP sequence |
| SEQ ID NO. 111 | SP-1 | GGGGCGGGGC | transcription factor recognition motif excluded from RenSP sequence |
| SEQ ID NO. 112 | SREBP-1 | TCACGTGA | transcription factor recognition motif excluded from RenSP sequence |

FIG. 3 (cont.)

| SEQ ID NO | Name | Sequence | Note |
|---|---|---|---|
| SEQ ID NO. 113 | SRF | GNCCAWATAWGG | transcription factor recognition motif excluded from RenSP sequence |
| SEQ ID NO. 114 | SRY | KTWGTTT | transcription factor recognition motif excluded from RenSP sequence |
| SEQ ID NO. 115 | STAT | TCCMAGAA | transcription factor recognition motif excluded from RenSP sequence |
| SEQ ID NO. 116 | STAT1 | CANTTCCS | transcription factor recognition motif excluded from RenSP sequence |
| SEQ ID NO. 117 | STAT5A | ATTTCC | transcription factor recognition motif excluded from RenSP sequence |
| SEQ ID NO. 118 | STATX | TTMCGGGAA | transcription factor recognition motif excluded from RenSP sequence |
| SEQ ID NO. 119 | T3R | MNTGWCCT | transcription factor recognition motif excluded from RenSP sequence |
| SEQ ID NO. 120 | TAL-1ALPHA/ E47 | AACAGATGKT | transcription factor recognition motif excluded from RenSP sequence |
| SEQ ID NO. 121 | TBP | TATAAA | transcription factor recognition motif excluded from RenSP sequence |
| SEQ ID NO. 122 | TCF-1(P) | GKCRGKTT | transcription factor recognition motif excluded from RenSP sequence |
| SEQ ID NO. 123 | TCF11 | WNNATGAC | transcription factor recognition motif excluded from RenSP sequence |
| SEQ ID NO. 124 | TCF-4 | WTCAAAGS | transcription factor recognition motif excluded from RenSP sequence |
| SEQ ID NO. 125 | TEF | TTATRTWAACAT | transcription factor recognition motif |

FIG. 3 (cont.)

| SEQ ID NO | Name | Sequence | Note |
|---|---|---|---|
| SEQ ID NO. 126 | TEL-2 | CAGGAAGTAR | transcription factor recognition motif excluded from RenSP sequence |
| SEQ ID NO. 127 | TFII-I | RGAGGKAGG | transcription factor recognition motif excluded from RenSP sequence |
| SEQ ID NO. 128 | YY1 | GCCATNTT | transcription factor recognition motif excluded from RenSP sequence |
| SEQ ID NO. 129 | ZID | GGCTCYATCAYC | transcription factor recognition motif excluded from RenSP sequence |
| SEQ ID NO. 130 | SMAD | GTCTAGAC | transcription factor recognition motif excluded from RenSP sequence |
| SEQ ID NO. 131 | ER | GGTCANNNTGACC | transcription factor recognition motif excluded from RenSP sequence |
| SEQ ID NO. 132 | GR | AGAACANNNTGTTCT | transcription factor recognition motif excluded from RenSP sequence |
| SEQ ID NO. 133 | PPAR | GGTCAAAGGTCA | transcription factor recognition motif excluded from RenSP sequence |
| SEQ ID NO. 134 | p53 | RRRCWWGYYY | transcription factor recognition motif excluded from RenSP sequence |
| SEQ ID NO. 135 | MLU1 | ACGCGT | restriction site excluded from RenSP sequence |
| SEQ ID NO. 136 | SAC1 | GAGCTC | restriction site excluded from RenSP sequence |
| SEQ ID NO. 137 | NHE1 | GCTAGC | restriction site excluded from RenSP sequence |
| SEQ ID NO. 138 | ACC651/ KPN1 | GGTACC | restriction site excluded from RenSP sequence |
| SEQ ID NO. 139 | AVR2 | CCTAGG | restriction site excluded from RenSP sequence |
| SEQ ID NO. 140 | XBA1 | TCTAGA | restriction site excluded from RenSP sequence |

FIG. 3 (cont.)

| SEQ ID NO | Name | Sequence | Note |
|---|---|---|---|
| SEQ ID NO. 141 | BGL2 | AGATCT | restriction site excluded from RenSP sequence |
| SEQ ID NO. 142 | HIND3 | AAGCTT | restriction site excluded from RenSP sequence |
| SEQ ID NO. 143 | XHO1 | CTCGAG | restriction site excluded from RenSP sequence |
| SEQ ID NO. 144 | XMA1 | CCCGGG | restriction site excluded from RenSP sequence |
| SEQ ID NO. 145 | FSE1 | GGCCGGCC | restriction site excluded from RenSP sequence |
| SEQ ID NO. 146 | AVR2 | CCTAGG | restriction site excluded from RenSP sequence |
| SEQ ID NO. 147 | SAL1 | GTCGAC | restriction site excluded from RenSP sequence |
| SEQ ID NO. 148 | ECOR1 | GAATTC | restriction site excluded from RenSP sequence |
| SEQ ID NO. 149 | BAMH1 | GGATCC | restriction site excluded from RenSP sequence |
| SEQ ID NO. 150 | RPL10 Promote | GTACCCGGTCACCTCTCTGATCTGCGCATGTGCTGGGCTACGC GCGGGCGCAAGCGCCAAGAGCGGCTGCGTCTATGGTCATGAC GTCTGACAGAGCGTCCACCCGTCTTCGACAGGACTCTATGGTT CTTACGCGCGCAGACAGACCGCCTATATAAGCCATGCGCAGG CGGAGGAGCGCCTCTTTCCCTTCGGTGTGGGGAGCAAGCGCA GTTGTCGTCTCTTGCGGTGCCGTCGCTGGTTCTCACACCTTTTA GGTCTGTTCTCGTCTTCC | strong constitutive eukaryotic promoter |
| SEQ ID NO. 151 | ACTB Promoter and 5'UTR multiple cloning site | ATAGCAGACATACAACGGACGGTGGGCCCAGACCCAGGCTGT GTAGACCCAGCCCCCCCGCCCCGCAGTGCCTAGGTCACCCACT AACGCCCCAGGCCTTGTCTTGGCTGGGCGTGACTGTTACCCTC AAAAGCAGGCAGCTCCAGGGTAAAAGGTGCCCTGCCCTGTAG AGCCCACCTTCCTTCCCAGGGCTGCGGCTGGGTAGGTTTGTAG CCTTCATCACGGGCCACCTCCAGCCACTGGACCGCTGGCCCCT GCCCTGTCCTGGGGAGTGTGGTCCTGCGACTTCTAAGTGGCCG CAAGCCACCTGACTCCCCCAACACCACACTCTACCTCTCAAGCC CAGGTCTCTCCCTAGTGACCCACCCAGCACATTTAGCTAGCTG AGCCCCACAGCCAGAGGTCCTCAGGCCCTGCTTTCAGGGCAGT TGCTCTGAAGTCGGCAAGGGGGAGTGACTGCCTGGCCACTCC ATGCCCTCCAAGAGCTCCTTCTGCAGGAGCGTACAGAACCCAG GGCCCTGGCACCCGTGCAGACCCTGGCCCACCCCACCTGGGC GCTCAGTGCCCAAGAGATGTCCACACCTAGGATGTCCCGCGGT GGGTGGGGGGCCCGAGAGACGGGCAGGCCGGGGGCAGGCC TGGCCATGCGGGGCCGAACCGGGCACTGCCCAGCGTggggcgc gggggccacggcgcgcgcccccagccccgggcccAGCACCCCAAGGCG GCCAACGCCAAAACTCTCCCTCCTCCTCTTCCTCAATCTCGCTCT CGCTCTTTTTTTTTTTTCGCAAAAGGAGGGGAGAGGGGGTAAAA AAATGCTGCACTGTGCGGCGAAGCCGGTGAGTGAGCGGCGC GGGGCCAATCAGCGTGCGCCGTTCCGAAAGTTGCCTTTTATGG CTCGAGCGGCCGCGGCGGCGCCCTATAAAACCCAGCGGCGCG ACGCGCCACCACCGCCGAGACCGCGTCCGCCCCGAGATCTCA GAGCCTCGCCTTTCTTAAGCCGATCCGCCGGACGTCCACACCC CCTGCAGGCTCACC | strong constitutive eukaryotic promoter with multiple cloning site for 5'UTR sequences |

FIG. 3 (cont.)

| SEQ ID NO | Name | Sequence | Note |
|---|---|---|---|
| SEQ ID NO. 152 | hRlucP | ATGGCTTCCAAGGTGTACGACCCCGAGCAACGCAAACGCATG ATCACTGGGCCTCAGTGGTGGGCTCGCTGCAAGCAAATGAAC GTGCTGGACTCCTTCATCAACTACTATGATTCCGAGAAGCACG CCGAGAACGCCGTGATTTTTCTGCATGGTAACGCTGCCTCCAG CTACCTGTGGAGGCACGTCGTGCCTCACATCGAGCCCGTGGCT AGATGCATCATCCCTGATCTGATCGGAATGGGTAAGTCCGGCA AGAGCGGGAATGGCTCATATCGCCTCCTGGATCACTACAAGTA CCTCACCGCTTGGTTCGAGCTGCTGAACCTTCCAAAGAAAATC ATCTTTGTGGGCCACGACTGGGGGGCTTGTCTGGCCTTTCACT ACTCCTACGAGCACCAAGACAAGATCAAGGCCATCGTCCATGC TGAGAGTGTCGTGGACGTGATCGAGTCCTGGGACGAGTGGCC TGACATCGAGGAGGATATCGCCCTGATCAAGAGCGAAGAGGG CGAGAAAATGGTGCTTGAGAATAACTTCTTCGTCGAGACCATG CTCCCAAGCAAGATCATGCGGAAACTGGAGCCTGAGGAGTTC GCTGCCTACCTGGAGCCATTCAAGGAGAAGGGCGAGGTTAGA CGGCCTACCCTCTCCTGGCCTCGCGAGATCCCTCTCGTTAAGG GAGGCAAGCCCGACGTCGTCCAGATTGTCCGCAACTACAACG CCTACCTTCGGGCCAGCGACGATCTGCCTAAGATGTTCATCGA GTCCGACCCTGGGTTCTTTTCCAACGCTATTGTCGAGGGAGCT AAGAAGTTCCCTAACACCGAGTTCGTGAAGGTGAAGGGCCTC CACTTCAGCCAGGAGGACGCTCCAGATGAAATGGGTAAGTAC ATCAAGAGCTTCGTGGAGCGCGTGCTGAAGAACGAGCAGAAT TCTCACGGCTTCCCTCCCGAGGTGGAGGAGCAGGCCGCCGGC ACCCTGCCCATGAGCTGCGCCCAGGAGAGCGGCATGGATAGA CACCCTGCTGCTTGCGCCAGCGCCAGGATCAACGTCTAA | humanized Renilla with PEST sequence |
| SEQ ID NO. 153 | hRluc | ATGGCTTCCAAGGTGTACGACCCCGAGCAACGCAAACGCATG ATCACTGGGCCTCAGTGGTGGGCTCGCTGCAAGCAAATGAAC GTGCTGGACTCCTTCATCAACTACTATGATTCCGAGAAGCACG CCGAGAACGCCGTGATTTTTCTGCATGGTAACGCTGCCTCCAG CTACCTGTGGAGGCACGTCGTGCCTCACATCGAGCCCGTGGCT AGATGCATCATCCCTGATCTGATCGGAATGGGTAAGTCCGGCA AGAGCGGGAATGGCTCATATCGCCTCCTGGATCACTACAAGTA CCTCACCGCTTGGTTCGAGCTGCTGAACCTTCCAAAGAAAATC ATCTTTGTGGGCCACGACTGGGGGGCTTGTCTGGCCTTTCACT ACTCCTACGAGCACCAAGACAAGATCAAGGCCATCGTCCATGC TGAGAGTGTCGTGGACGTGATCGAGTCCTGGGACGAGTGGCC TGACATCGAGGAGGATATCGCCCTGATCAAGAGCGAAGAGGG CGAGAAAATGGTGCTTGAGAATAACTTCTTCGTCGAGACCATG CTCCCAAGCAAGATCATGCGGAAACTGGAGCCTGAGGAGTTC GCTGCCTACCTGGAGCCATTCAAGGAGAAGGGCGAGGTTAGA CGGCCTACCCTCTCCTGGCCTCGCGAGATCCCTCTCGTTAAGG GAGGCAAGCCCGACGTCGTCCAGATTGTCCGCAACTACAACG CCTACCTTCGGGCCAGCGACGATCTGCCTAAGATGTTCATCGA GTCCGACCCTGGGTTCTTTTCCAACGCTATTGTCGAGGGAGCT AAGAAGTTCCCTAACACCGAGTTCGTGAAGGTGAAGGGCCTC CACTTCAGCCAGGAGGACGCTCCAGATGAAATGGGTAAGTAC ATCAAGAGCTTCGTGGAGCGCGTGCTGAAGAACGAGCAGTAA | humanized Renilla |

FIG. 3 (cont.)

SEQUENCE LISTING

```
<160> NUMBER OF SEQ ID NOS: 153

<210> SEQ ID NO 1
<211> LENGTH: 311
<212> TYPE: PRT
<213> ORGANISM: Artificial Sequence
<220> FEATURE:
<223> OTHER INFORMATION: Optimized Renilla without Pest sequence

<400> SEQUENCE: 1

Met Ala Ser Lys Val Tyr Asp Pro Glu Gln Arg Lys Arg Met Ile Thr
 1               5                  10                  15

Gly Pro Gln Trp Trp Ala Arg Cys Lys Gln Met Asn Val Leu Asp Ser
             20                  25                  30

Phe Ile Asn Tyr Tyr Asp Ser Glu Lys His Ala Glu Asn Ala Val Ile
         35                  40                  45

Phe Leu His Gly Asn Ala Ala Ser Ser Tyr Leu Trp Arg His Val Val
     50                  55                  60

Pro His Ile Glu Pro Val Ala Arg Cys Ile Ile Pro Asp Leu Ile Gly
 65                  70                  75                  80

Met Gly Lys Ser Gly Lys Ser Gly Asn Gly Ser Tyr Arg Leu Leu Asp
                 85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Cys Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Met Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
```

```
                        210                 215                 220
Leu Val Lys Gly Gly Lys Pro Asp Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310

<210> SEQ ID NO 2
<211> LENGTH: 978
<212> TYPE: DNA
<213> ORGANISM: Artificial Sequence
<220> FEATURE:
<223> OTHER INFORMATION: Optimized Renilla without Pest sequence

<400> SEQUENCE: 2
aagcttggca ttccggtact gttggtaaag ccaccatggc ttccaaggtg tacgacccgg    60
agcagcgcaa gaggatgatc accggccctc agtggtgggc tcggtgcaag cagatgaacg   120
tgctcgactc cttcatcaac tactacgaca gcgagaaaca tgcggagaac gccgtgatct   180
tcctccacgg caacgccgct tcctcctacc tgtggcgcca cgtcgtgccc cacatcgagc   240
ccgtcgcccg gtgcatcatc cctgatctga tcgggatggg gaagagcggg aagagcggca   300
acggcagcta ccgcctgctc gaccactaca gtacctcac cgcctggttc gagctgctga   360
acctccccaa gaagatcatc tttgtgggcc acgactgggg cgcttgtctc gcttttcact   420
actcctacga gcaccaggat aagatcaagg ctatcgtgca tgctgagagc gtcgtggacg   480
tgatcgagtc ctgggacgag tggcccgata tcgaggagga tattgctctg atcaagtccg   540
aggagggcga gaagatggtc ctggagaata acttcttcgt ggagactatg ctgcctagca   600
agatcatgcg caagctggag cccgaggagt tcgctgctta cctggagccc ttcaaggaga   660
agggcgaggt cagaagacca accctcagct ggcctcggga gatccctctg gtcaagggcg   720
ggaagccgga cgtggtgcag atcgtccgga actacaacgc ctacctgcgc gccagcgacg   780
acctgcctaa gatgttcatc gagtccgacc ccggcttctt cagcaacgct atcgtggagg   840
gcgccaagaa gttccccaac accgagttcg tgaaggtgaa gggcctccac ttctcccaag   900
aggacgcccc tgatgagatg gggaagtaca tcaagagctt cgtcgagcgc gtcctcaaga   960
acgagcagta attctaga                                                  978

<210> SEQ ID NO 3
<211> LENGTH: 352
<212> TYPE: PRT
<213> ORGANISM: Artificial Sequence
<220> FEATURE:
<223> OTHER INFORMATION: Optimized Renilla with Pest sequence

<400> SEQUENCE: 3

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30
```

Phe Ile Asn Tyr Tyr Asp Ser Glu Lys His Ala Glu Asn Ala Val Ile
                35                  40                  45

Phe Leu His Gly Asn Ala Ala Ser Ser Tyr Leu Trp Arg His Val Val
     50                  55                  60

Pro His Ile Glu Pro Val Ala Arg Cys Ile Ile Pro Asp Leu Ile Gly
 65                  70                  75                  80

Met Gly Lys Ser Gly Lys Ser Gly Asn Gly Ser Tyr Arg Leu Leu Asp
                 85                  90                  95

His Tyr Lys Tyr Leu Thr Ala Trp Phe Glu Leu Leu Asn Leu Pro Lys
                100                 105                 110

Lys Ile Ile Phe Val Gly His Asp Trp Gly Ala Cys Leu Ala Phe His
            115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Gly Glu Lys Met Val Leu
                165                 170                 175

Glu Asn Asn Phe Phe Val Glu Thr Met Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln Asn Ser His Gly Phe Pro Pro Glu Val
305                 310                 315                 320

Glu Glu Gln Ala Ala Gly Thr Leu Pro Met Ser Cys Ala Gln Glu Ser
                325                 330                 335

Gly Met Asp Arg His Pro Ala Ala Cys Ala Ser Ala Arg Ile Asn Val
            340                 345                 350

<210> SEQ ID NO 4
<211> LENGTH: 1100
<212> TYPE: DNA
<213> ORGANISM: Artificial Sequence
<220> FEATURE:
<223> OTHER INFORMATION: Optimized Renilla with Pest sequence

<400> SEQUENCE: 4
aagcttggca ttccggtact gttggtaaag ccaccatggc ttccaaggtg tacgacccgg      60
agcagcgcaa gaggatgatc accggccctc agtggtgggc tcggtgcaag cagatgaacg     120
tgctcgactc cttcatcaac tactacgaca gcgagaaaca tgcggagaac gccgtgatct     180
tcctccacgg caacgccgct tcctcctacc tgtggcgcca cgtcgtgccc cacatcgagc     240

```
ccgtcgcccg gtgcatcatc cctgatctga tcgggatggg gaagagcggg aagagcggca      300
acggcagcta ccgcctgctc gaccactaca agtacctcac cgcctggttc gagctgctga      360
acctccccaa gaagatcatc tttgtgggcc acgactgggg cgcttgtctc gcttttcact      420
actcctacga gcaccaggat aagatcaagg ctatcgtgca tgctgagagc gtcgtggacg      480
tgatcgagtc ctgggacgag tggcccgata tcgaggagga tattgctctg atcaagtccg      540
aggagggcga gaagatggtc ctggagaata acttcttcgt ggagactatg ctgcctagca      600
agatcatgcg caagctggag cccgaggagt tcgctgctta cctggagccc ttcaaggaga      660
agggcgaggt cagaagacca accctcagct ggcctcggga gatccctctg gtcaagggcg      720
ggaagccgga cgtggtgcag atcgtccgga actacaacgc ctacctgcgc gccagcgacg      780
acctgcctaa gatgttcatc gagtccgacc ccggcttctt cagcaacgct atcgtggagg      840
gcgccaagaa gttccccaac accgagttcg tgaaggtgaa gggcctccac ttctcccaag      900
aggacgcccc tgatgagatg gggaagtaca tcaagagctt cgtcgagcgc gtcctcaaga      960
acgagcagaa ttctcacggc ttccctcccg aggtggagga gcaggccgcc ggcaccctgc     1020
ccatgagctg cgcccaggag agcggcatgg atagacaccc tgctgcttgc gccagcgcca     1080
ggatcaacgt ctaatctaga                                                 1100
```

<210> SEQ ID NO 5
<211> LENGTH: 3656
<212> TYPE: DNA
<213> ORGANISM: Artificial Sequence
<220> FEATURE:
<223> OTHER INFORMATION: Promoter reporter vector with optimized Renilla lucierase with PEST sequence

<400> SEQUENCE: 5

```
ggcctaactg gccggtacct gagctcttac gcgtgctagc ccgggctcga gatctgcgat      60
ctaagtaagc ttaactaagt aaggcattcc ggtactgttg gtaaagccac catggcttcc     120
aaggtgtacg acccggagca gcgcaagagg atgatcaccg ccctcagtg gtgggctcgg     180 tgcaagcaga tgaacgtgct cgactccttc atcaactact acgacagcga gaaacatgcg     240
gagaacgccg tgatcttcct ccacggcaac gccgcttcct cctacctgtg cgccacgtc     300 gtgccccaca tcgagcccgt cgcccggtgc atcatccctg atctgatcgg gatggggaag     360
agcgggaaga gcggcaacgg cagctaccgc ctgctcgacc actacaagta cctcaccgcc     420
tggttcgagc tgctgaacct ccccaagaag atcatctttg tgggccacga ctggggcgct     480
tgtctcgctt tcactactc ctacgagcac caggataaga tcaaggctat cgtgcatgct     540
gagagcgtcg tggacgtgat cgagtcctgg gacgagtggc ccgatatcga ggaggatatt     600
gctctgatca agtccgagga gggcgagaag atggtcctgg agaataactt cttcgtggag     660
actatgctgc ctagcaagat catgcgcaag ctggagcccg aggagttcgc tgcttacctg     720
gagcccttca aggagaaggg cgaggtcaga agaccaaccc tcagctggcc tcgggagatc     780
cctctggtca agggcgggaa gccggacgtg gtgcagatcg tccggaacta caacgcctac     840
ctgcgcgcca gcgacgacct gcctaagatt ttcatcgagt ccgacccagg cttcttcagc     900
aacgctatcg tggagggcgc caagaagttc cccaacaccg agttcgtgaa ggtgaagggc     960
ctccacttct cccaagagga cgcccctgat gagatgggga agtacatcaa gagcttcgtc    1020
gagcgcgtcc tcaagaacga gcagaattct cacggcttcc ctcccgaggt ggaggagcag    1080
gccgccggca ccctgcccat gagctgcgcc caggagagcg gcatggatag acaccctgct    1140
```

```
gcttgcgcca gcgccaggat caacgtctaa tctagagtcg gggcggccgg ccgcttcgag   1200
cagacatgat aagatacatt gatgagtttg gacaaaccac aactagaatg cagtgaaaaa   1260
aatgctttat ttgtgaaatt tgtgatgcta ttgctttatt tgtaaccatt ataagctgca   1320
ataaacaagt taacaacaac aattgcattc attttatgtt tcaggttcag ggggaggtgt   1380
gggaggtttt ttaaagcaag taaaacctct acaaatgtgg taaaatcgat aaggatccgt   1440
cgaccgatgc ccttgagagc cttcaaccca gtcagctcct tccggtgggc gcggggcatg   1500
actatcgtcg ccgcacttat gactgtcttc tttatcatgc aactcgtagg acaggtgccg   1560
gcagcgctct tccgcttcct cgctcactga ctcgctgcgc tcggtcgttc ggctgcggcg   1620
agcggtatca gctcactcaa aggcggtaat acggttatcc acagaatcag gggataacgc   1680
aggaaagaac atgtgagcaa aaggccagca aaaggccagg aaccgtaaaa aggccgcgtt   1740
gctggcgttt ttccataggc tccgcccccc tgacgagcat cacaaaaatc gacgctcaag   1800
tcagaggtgg cgaaacccga caggactata aagataccag gcgtttcccc ctggaagctc   1860
cctcgtgcgc tctcctgttc cgaccctgcc gcttaccgga tacctgtccg cctttctccc   1920
ttcgggaagc gtggcgcttt ctcatagctc acgctgtagg tatctcagtt cggtgtaggt   1980
cgttcgctcc aagctgggct gtgtgcacga accccccgtt cagcccgacc gctgcgcctt   2040
atccggtaac tatcgtcttg agtccaaccc ggtaagacac gacttatcgc cactggcagc   2100
agccactggt aacaggatta gcagagcgag gtatgtaggc ggtgctacag agttcttgaa   2160
gtggtggcct aactacggct acactagaag aacagtattt ggtatctgcg ctctgctgaa   2220
gccagttacc ttcggaaaaa gagttggtag ctcttgatcc ggcaaacaaa ccaccgctgg   2280
tagcggtggt ttttttgttt gcaagcagca gattacgcgc agaaaaaaag gatctcaaga   2340
agatcctttg atcttttcta cggggtctga cgctcagtgg aacgaaaact cacgttaagg   2400
gattttggtc atgagattat caaaaaggat cttcacctag atcctttaa attaaaaatg   2460 aagttttaaa tcaatctaaa gtatatatga gtaaacttgg tctgacagcg gccgcaaatg   2520
ctaaaccact gcagtggtta ccaatgctta atcagtgagg cacctatctc agcgatctgt   2580
ctatttcgtt catccatagt tgcctgactc cccgtcgtgt agataactac gatacgggag   2640
ggcttaccat ctggccccag cgctgcgatg ataccgcgag aaccacgctc accggctccg   2700
gatttatcag caataaacca gccagccgga agggccgagc gcagaagtgg tcctgcaact   2760
ttatccgcct ccatccagtc tattaattgt tgccgggaag ctagagtaag tagttcgcca   2820
gttaatagtt tgcgcaacgt tgttgccatc gctacaggca tcgtggtgtc acgctcgtcg   2880
tttggtatgg cttcattcag ctccggttcc caacgatcaa ggcgagttac atgatccccc   2940
atgttgtgca aaaaagcggt tagctccttc ggtcctccga tcgttgtcag aagtaagttg   3000
gccgcagtgt tatcactcat ggttatggca gcactgcata attctcttac tgtcatgcca   3060
tccgtaagat gcttttctgt gactggtgag tactcaacca agtcattctg agaatagtgt   3120
atgcggcgac cgagttgctc ttgcccggcg tcaatacggg ataataccgc gccacatagc   3180
agaactttaa aagtgctcat cattggaaaa cgttcttcgg ggcgaaaact ctcaaggatc   3240
ttaccgctgt tgagatccag ttcgatgtaa cccactcgtg cacccaactg atcttcagca   3300
tcttttactt tcaccagcgt ttctgggtga gcaaaaacag gaaggcaaaa tgccgcaaaa   3360
aagggaataa gggcgacacg gaaatgttga atactcatac tcgtcctttt tcaatattat   3420
tgaagcattt atcagggtta ctagtacgtc tctcaaggat aagtaagtaa tattaaggta   3480
cgggaggtat tggacaggcc gcaataaaat atctttattt tcattacatc tgtgtgttgg   3540
```

```
tttttttgtgt gaatcgatag tactaacata cgctctccat caaaacaaaa cgaaacaaaa    3600
caaactagca aaataggctg tccccagtgc aagtgcaggt gccagaacat ttctct         3656

<210> SEQ ID NO 6
<211> LENGTH: 3910
<212> TYPE: DNA
<213> ORGANISM: Artificial Sequence
<220> FEATURE:
<223> OTHER INFORMATION: 3'UTR reporter vector with optimized Renilla
      lucierase with PEST sequence

<400> SEQUENCE: 6
ggcctaactg gccggtacct gagctcacgc gtgtacccgg tcacctctct gatctgcgca      60
tgtgctgggc tacgcgcggg cgcaagcgcc aagagcggct gcgtctatgg tcatgacgtc     120
tgacagagcg tccacccgtc ttcgacagga ctctatggtt cttacgcgcg cagacagacc     180
gcctatataa gccatgcgca ggcggaggag cgcctctttc ccttcggtgt ggggagcaag     240
cgcagttgtc gtctcttgcg gtgccgtcgc tggttctcac accttttagg tctgttctcg     300
tcttcccgag atctaagctt ggcattccgg tactgttggt aaagccacca tggcttccaa     360
ggtgtacgac ccggagcagc gcaagaggat gatcaccggc cctcagtggt gggctcggtg     420
caagcagatg aacgtgctcg actccttcat caactactac gacagcgaga acatgcgga     480 gaacgccgtg atcttcctcc acggcaacgc cgcttcctcc tacctgtggc gccacgtcgt     540
gccccacatc gagcccgtcg cccggtgcat catccctgat ctgatcggga tggggaagag     600
cgggaagagc ggcaacggca gctaccgcct gctcgaccac tacaagtacc tcaccgcctg     660
gttcgagctg ctgaacctcc ccaagaagat catctttgtg ggccacgact ggggcgcttg     720
tctcgctttt cactactcct acgagcacca ggataagatc aaggctatcg tgcatgctga     780
gagcgtcgtg gacgtgatcg agtcctggga cgagtggccc gatatcgagg aggatattgc     840
tctgatcaag tccgaggagg gcgagaagat ggtcctggag aataacttct cgtggagac      900 tatgctgcct agcaagatca tgcgcaagct ggagcccgag gagttcgctg cttacctgga     960
gcccttcaag gagaagggcg aggtcagaag accaacccct cagctggcct gggagatccc    1020
tctggtcaag ggcgggaagc cggacgtggt gcagatcgtc cggaactaca acgcctacct    1080
gcgcgccagc gacgacctgc ctaagatgtt catcgagtcc gaccccggct tcttcagcaa    1140
cgctatcgtg gagggcgcca agaagttccc caacaccgag ttcgtgaagg tgaagggcct    1200
ccacttctcc caagaggacg cccctgatga gatggggaag tacatcaaga gcttcgtcga    1260
gcgcgtcctc aagaacgagc agaattctca cggcttccct cccgaggtgg aggagcaggc    1320
cgccggcacc ctgcccatga gctgcgccca ggagagcggc atggatagac ccctgctgc     1380 ttgcgccagc gccaggatca acgtctaatc tagagctagc cctagggata tcctcgaggg    1440
ccggccgctt cgagcagaca tgataagata cattgatgag tttggacaaa ccacaactag    1500
aatgcagtga aaaaaatgct ttatttgtga aatttgtgat gctattgctt tatttgtaac    1560
cattataagc tgcaataaac aagttaacaa caacaattgc attcatttta tgtttcaggt    1620 tcaggggag gtgtgggagg ttttttaaag caagtaaaac ctctacaaat gtggtaaaat    1680
cgataaggat ccgtcgaccg atgcccttga gagccttcaa cccagtcagc tccttccggt    1740
gggcgcgggg catgactatc gtcgccgcac ttatgactgt cttctttatc atgcaactcg    1800
taggacaggt gccggcagcg ctcttccgct tcctcgctca ctgactcgct gcgctcggtc    1860
gttcggctgc ggcgagcggt atcagctcac tcaaaggcgg taatacggtt atccacagaa    1920
```

-continued

```
tcaggggata acgcaggaaa gaacatgtga gcaaaaggcc agcaaaaggc caggaaccgt    1980
aaaaaggccg cgttgctggc gttttttccat aggctccgcc ccctgacga gcatcacaaa    2040 aatcgacgct caagtcagag gtggcgaaac ccgacaggac tataaagata ccaggcgttt    2100
ccccctggaa gctccctcgt gcgctctcct gttccgaccc tgccgcttac cggatacctg    2160
tccgcctttc tcccttcggg aagcgtggcg ctttctcata gctcacgctg taggtatctc    2220
agttcggtgt aggtcgttcg ctccaagctg ggctgtgtgc acgaaccccc cgttcagccc    2280
gaccgctgcg ccttatccgg taactatcgt cttgagtcca acccggtaag acacgactta    2340
tcgccactgg cagcagccac tggtaacagg attagcagag cgaggtatgt aggcggtgct    2400
acagagttct tgaagtggtg gcctaactac ggctacacta agaacagt atttggtatc      2460 tgcgctctgc tgaagccagt taccttcgga aaagagttg gtagctcttg atccggcaaa    2520
caaaccaccg ctggtagcgg tggtttttttt gtttgcaagc agcagattac gcgcagaaaa    2580
aaaggatctc aagaagatcc tttgatcttt tctacgggt ctgacgctca gtggaacgaa     2640
aactcacgtt aagggatttt ggtcatgaga ttatcaaaaa ggatcttcac ctagatcctt    2700
ttaaattaaa aatgaagttt taaatcaatc taaagtatat atgagtaaac ttggtctgac    2760
agcggccgca aatgctaaac cactgcagtg gttaccaatg cttaatcagt gaggcaccta    2820
tctcagcgat ctgtctattt cgttcatcca tagttgcctg actccccgtc gtgtagataa    2880
ctacgatacg ggagggctta ccatctggcc ccagcgctgc gatgataccg cgagaaccac    2940
gctcaccggc tccggattta tcagcaataa accagccagc cggaagggcc gagcgcagaa    3000
gtggtcctgc aactttatcc gcctccatcc agtctattaa ttgttgccgg gaagctagag    3060
taagtagttc gccagttaat agtttgcgca acgttgttgc catcgctaca ggcatcgtgg    3120
tgtcacgctc gtcgtttggt atggcttcat tcagctccgg ttcccaacga tcaaggcgag    3180
ttacatgatc ccccatgttg tgcaaaaaag cggttagctc cttcggtcct ccgatcgttg    3240
tcagaagtaa gttggccgca gtgttatcac tcatggttat ggcagcactg cataattctc    3300
ttactgtcat gccatccgta agatgctttt ctgtgactgg tgagtactca accaagtcat    3360
tctgagaata gtgtatgcgg cgaccgagtt gctcttgccc ggcgtcaata cgggataata    3420
ccgcgccaca tagcagaact ttaaaagtgc tcatcattgg aaaacgttct cggggcgaa    3480 aactctcaag gatcttaccg ctgttgagat ccagttcgat gtaacccact cgtgcaccca    3540
actgatcttc agcatctttt actttcacca gcgtttctgg gtgagcaaaa acaggaaggc    3600
aaaatgccgc aaaaaaggga ataagggcga cacggaaatg ttgaatactc atactcgtcc    3660 ttttttcaata ttattgaagc atttatcagg gttactagta cgtctctcaa ggataagtaa    3720
gtaatattaa ggtacgggag gtattggaca ggccgcaata aaatatcttt attttcatta    3780
catctgtgtg ttggttttttt gtgtgaatcg atagtactaa catacgctct ccatcaaaac    3840
aaaacgaaac aaaacaaact agcaaaatag gctgtcccca gtgcaagtgc aggtgccaga    3900
acatttctct                                                            3910
```

<210> SEQ ID NO 7
<211> LENGTH: 3846
<212> TYPE: DNA
<213> ORGANISM: Artificial Sequence
<220> FEATURE:
<223> OTHER INFORMATION: Long-range element reporter vector with optimized Renilla lucierase with PEST sequence

<400> SEQUENCE: 7

```
ggcctaactg gccggtacct gagctcttac gcgtgctagc ccgggctcga gatctgcgat      60
ctaagtaagc ttcgtttgct ggcggtgtcc ccggaagaaa tatatttgca tgtctttagt     120
tctatgatga cacaaacccc gcccagcgtc ttgtcattgg cgaattcgaa cacgcagatg     180
cagtcggggc ggcgcggtcc caggtccact tcgcatatta aggtgacgcg cgtggcctcg     240
aacaccgagc gaccctgcag cgacccgctt aaggcaatcc ggtactgttg gtaaagccac     300
catggcttcc aaggtatacg acccggagca gcgcaagagg atgatcaccg gccctcagtg     360
gtgggctcgg tgcaagcaga tgaacgtgct cgactccttc atcaactact acgacagcga     420
gaaacatgcg gagaacgccg tgatcttcct ccacggcaac gccgcttcct cctacctgtg     480
gcgccacgtc gtgccccaca tcgagcccgt cgcccggtgc atcatccctg atctgatcgg     540
gatggggaag agcgggaaga gcggcaacgg cagctaccgc ctgctcgacc actacaagta     600
cctcaccgcc tggttcgagc tgctgaacct ccccaagaag atcatctttg tgggccacga     660
ctggggcgct tgtctcgctt ttcactactc ctacgagcac caggataaga tcaaggctat     720
cgtgcatgct gagagcgtcg tggacgtgat cgagtcctgg gacgagtggc ccgatatcga     780
ggaggatatt gctctgatca agtccgagga gggcgagaag atggtcctgg agaataactt     840
cttcgtggag actatgctgc ctagcaagat catgcgcaag ctggagcccg aggagttcgc     900
tgcttacctg gagcccttca aggagaaggg cgaggtcaga agaccaaccc tcagctggcc     960
tcgggagatc cctctggtca agggcgggaa gccggacgtg gtgcagatcg tccggaacta    1020
caacgcctac ctgcgcgcca gcgacgacct gcctaagatg ttcatcgagt ccgaccccgg    1080
cttcttcagc aacgctatcg tggagggcgc caagaagttc cccaacaccg agttcgtgaa    1140
ggtgaagggc ctccacttct cccaagagga cgccccctga gagatgggga agtacatcaa    1200
gagcttcgtc gagcgcgtcc tcaagaacga gcagaattct cacggcttcc ctcccgaggt    1260
ggaggagcag gccgccggca ccctgcccat gagctgcgcc caggagagcg gcatggatag    1320
acaccctgct gcttgcgcca gcgccaggat caacgtctaa tctagagtcg gggcggccgg    1380
ccgcttcgag cagacatgat aagatacatt gatgagtttg gacaaaccac aactagaatg    1440
cagtgaaaaa aatgctttat ttgtgaaatt tgtgatgcta ttgctttatt tgtaaccatt    1500
ataagctgca ataaacaagt taacaacaac aattgcattc attttatgtt tcaggttcag    1560
ggggaggtgt gggaggtttt ttaaagcaag taaaacctct acaaatgtgg taaaatcgat    1620
aaggatccgt cgaccgatgc ccttgagagc cttcaaccca gtcagctcct tccggtgggc    1680
gcggggcatg actatcgtcg ccgcacttat gactgtcttc tttatcatgc aactcgtagg    1740
acaggtgccg gcagcgctct tccgcttcct cgctcactga ctcgctgcgc tcggtcgttc    1800
ggctgcggcg agcggtatca gctcactcaa aggcggtaat acggttatcc acagaatcag    1860
gggataacgc aggaaagaac atgtgagcaa aaggccagca aaaggccagg aaccgtaaaa    1920
aggccgcgtt gctggcgttt ttccataggc tccgcccccc tgacgagcat cacaaaaatc    1980
gacgctcaag tcagaggtgg cgaaacccga caggactata aagataccag gcgtttcccc    2040
ctggaagctc cctcgtgcgc tctcctgttc cgaccctgcc gcttaccgga tacctgtccg    2100
cctttctccc ttcgggaagc gtggcgcttt ctcatagctc acgctgtagg tatctcagtt    2160
cggtgtaggt cgttcgctcc aagctgggct gtgtgcacga accccccgtt cagcccgacc    2220
gctgcgcctt atccggtaac tatcgtcttg agtccaaccc ggtaagacac gacttatcgc    2280
cactggcagc agccactggt aacaggatta gcagagcgag gtatgtaggc ggtgctacag    2340
```

-continued

```
agttcttgaa gtggtggcct aactacggct acactagaag aacagtattt ggtatctgcg    2400
ctctgctgaa gccagttacc ttcggaaaaa gagttggtag ctcttgatcc ggcaaacaaa    2460
ccaccgctgg tagcggtggt ttttttgttt gcaagcagca gattacgcgc agaaaaaaag    2520
gatctcaaga agatcctttg atcttttcta cggggtctga cgctcagtgg aacgaaaact    2580
cacgttaagg gattttggtc atgagattat caaaaaggat cttcacctag atccttttaa    2640
attaaaaatg aagttttaaa tcaatctaaa gtatatatga gtaaacttgg tctgacagcg    2700
gccgcaaatg ctaaaccact gcagtggtta ccaatgctta atcagtgagg cacctatctc    2760
agcgatctgt ctatttcgtt catccatagt tgcctgactc cccgtcgtgt agataactac    2820
gatacgggag ggcttaccat ctggccccag cgctgcgatg ataccgcgag aaccacgctc    2880
accggctccg gatttatcag caataaacca gccagccgga agggccgagc gcagaagtgg    2940
tcctgcaact ttatccgcct ccatccagtc tattaattgt tgccgggaag ctagagtaag    3000
tagttcgcca gttaatagtt tgcgcaacgt tgttgccatc gctacaggca tcgtggtgtc    3060
acgctcgtcg tttggtatgg cttcattcag ctccggttcc caacgatcaa ggcgagttac    3120
atgatccccc atgttgtgca aaaaagcggt tagctccttc ggtcctccga tcgttgtcag    3180
aagtaagttg gccgcagtgt tatcactcat ggttatggca gcactgcata attctcttac    3240
tgtcatgcca tccgtaagat gcttttctgt gactggtgag tactcaacca agtcattctg    3300
agaatagtgt atgcggcgac cgagttgctc ttgcccggcg tcaatacggg ataatacggc    3360
gccacatagc agaactttaa aagtgctcat cattggaaaa cgttcttcgg ggcgaaaact    3420
ctcaaggatc ttaccgctgt tgagatccag ttcgatgtaa cccactcgtg cacccaactg    3480
atcttcagca tcttttactt tcaccagcgt ttctgggtga gcaaaaacag gaaggcaaaa    3540
tgccgcaaaa aagggaataa gggcgacacg gaaatgttga atactcatac tcgtcctttt    3600
tcaatattat tgaagcattt atcagggtta ctagtacgtc tctcaaggat aagtaagtaa    3660
tattaaggta cggaggtat tggacaggcc gcaataaaat atctttatt tcattacatc    3720 tgtgtgttgg ttttttgtgt gaatcgatag tactaacata cgctctccat caaaacaaaa    3780
cgaaacaaaa caaactagca aaataggctg tccccagtgc aagtgcaggt gccagaacat    3840
ttctct                                                                3846
```

<210> SEQ ID NO 8
<211> LENGTH: 4624
<212> TYPE: DNA
<213> ORGANISM: Artificial Sequence
<220> FEATURE:
<223> OTHER INFORMATION: 5'UTR reporter vector with optimized Renilla
      lucierase with PEST sequence

<400> SEQUENCE: 8

```
ggcctaactg gccggtacct gagctcttac gcgtatagca gacatacaac ggacggtggg      60
cccagaccca ggctgtgtag acccagcccc ccgccccgc agtgcctagg tcacccacta     120
acgccccagg ccttgtcttg gctgggcgtg actgttaccc tcaaaagcag gcagctccag     180
ggtaaaaggt gccctgccct gtagagccca ccttccttcc cagggctgcg gctgggtagg     240
tttgtagcct tcatcacggg ccacctccag ccactggacc gctggcccct gcctgtcct      300 ggggagtgtg gtcctgcgac ttctaagtgg ccgcaagcca cctgactccc caacaccac     360 actctacctc tcaagcccag gtctctccct agtgacccac ccagcacatt tagctagctg     420
agccccacag ccagaggtcc tcaggccctg ctttcagggc agttgctctg aagtcggcaa     480
```

-continued

```
ggggggagtga ctgcctggcc actccatgcc ctccaagagc tccttctgca ggagcgtaca      540
gaacccaggg ccctggcacc cgtgcagacc ctggcccacc ccacctgggc gctcagtgcc      600
caagagatgt ccacacctag gatgtcccgc ggtgggtggg gggcccgaga cgggcagg       660 ccggggggcag gcctggccat gcggggccga accgggcact gcccagcgtg gggcgcgggg     720
gccacggcgc gcgcccccag cccccgggcc cagcacccca aggcggccaa cgccaaaact     780
ctccctcctc ctcttcctca atctcgctct cgctcttttt ttttttcgca aaggagggg      840 agagggggta aaaaaatgct gcactgtgcg gcgaagccgc tgagtgagcg gcgcgggggcc    900 aatcagcgtg cgccgttccg aaagttgcct tttatggctc gagcggccgc ggcggcgccc    960
tataaaaccc agcggcgcga cgcgccacca ccgccgagac cgcgtccgcc ccgagatctc    1020
agagcctcgc ctttcttaag ccgatccgcc ggacgtccac accccctgca ggctcaccca    1080
tggcttccaa ggtgtacgac ccggagcagc gcaagaggat gatcaccggc cctcagtggt    1140
gggctcggtg caagcagatg aacgtgctcg actccttcat caactactac gacagcgaga    1200
aacatgcgga gaacgccgtg atcttcctcc acggcaacgc cgcttcctcc tacctgtggc    1260
gccacgtcgt gccccacatc gagcccgtcg cccggtgcat catccctgat ctgatcggga    1320
tggggaagag cgggaagagc ggcaacggca gctaccgcct gctcgaccac tacaagtacc    1380
tcaccgcctg gttcgagctg ctgaacctcc ccaagaagat catctttgtg ggccacgact    1440
ggggcgcttg tctcgctttt cactactcct acgagcacca ggataagatc aaggctatcg    1500
tgcatgctga gagcgtcgtg gacgtgatcg agtcctggga cgagtggccc gatatcgagg    1560
aggatattgc tctgatcaag tccgaggagg gcgagaagat ggtcctggag aataacttct    1620
tcgtggagac tatgctgcct agcaagatca tgcgcaagct ggagcccgag gagttcgctg    1680
cttacctgga gcccttcaag gagaagggcg aggtcagaag accaacccct cagctggcctc    1740 gggagatccc tctggtcaag ggcgggaagc cggacgtggt gcagatcgtc cggaactaca    1800
acgcctacct gcgcgccagc gacgacctgc ctaagatgtt catcgagtcc gaccccggct    1860
tcttcagcaa cgctatcgtg gagggcgcca agaagttccc caacaccgag ttcgtgaagg    1920
tgaagggcct ccacttctcc caagaggacg cccctgatga gatggggaag tacatcaaga    1980
gcttcgtcga gcgcgtcctc aagaacgagc agaattctca cggcttccct cccgaggtgg    2040
aggagcaggc cgccggcacc ctgcccatga gctgcgccca ggagagcggc atggatagac    2100
accctgctgc ttgcgccagc gccaggatca acgtctaatc tagagtcggg gcggccggcc    2160
gcttcgagca gacatgataa gatacattga tgagtttgga caaaccacaa ctagaatgca    2220
gtgaaaaaaa tgctttattt gtgaaatttg tgatgctatt gctttatttg taaccattat    2280
aagctgcaat aaacaagtta acaacaacaa ttgcattcat tttatgtttc aggttcaggg    2340
ggaggtgtgg gaggtttttt aaagcaagta aaacctctac aaatgtggta aaatcgataa    2400
ggatccgtcg accgatgccc ttgagagcct tcaacccagt cagctccttc cggtgggcgc    2460
ggggcatgac tatcgtcgcc gcacttatga ctgtcttctt tatcatgcaa ctcgtaggac    2520
aggtgccggc agcgctcttc cgcttcctcg ctcactgact cgctgcgctc ggtcgttcgg    2580
ctgcggcgag cggtatcagc tcactcaaag gcggtaatac ggttatccac agaatcaggg    2640
gataacgcag gaaagaacat gtgagcaaaa ggccagcaaa aggccaggaa ccgtaaaaag    2700
gccgcgttgc tggcgttttt ccataggctc cgcccccctg acgagcatca caaaaatcga    2760
cgctcaagtc agaggtggcg aaacccgaca ggactataaa gataccaggc gtttcccccct    2820 ggaagctccc tcgtgcgctc tcctgttccg accctgccgc ttaccggata cctgtccgcc    2880
```

```
tttctccctt cgggaagcgt ggcgctttct catagctcac gctgtaggta tctcagttcg    2940
gtgtaggtcg ttcgctccaa gctgggctgt gtgcacgaac cccccgttca gcccgaccgc    3000
tgcgccttat ccgtaacta tcgtcttgag tccaacccgg taagacacga cttatcgcca    3060
ctggcagcag ccactggtaa caggattagc agagcgaggt atgtaggcgg tgctacagag    3120
ttcttgaagt ggtggcctaa ctacggctac actagaagaa cagtatttgg tatctgcgct    3180
ctgctgaagc cagttacctt cggaaaaaga gttggtagct cttgatccgg caaacaaacc    3240
accgctggta gcggtggttt ttttgtttgc aagcagcaga ttacgcgcag aaaaaaagga    3300
tctcaagaag atcctttgat cttttctacg ggtctgacg ctcagtggaa cgaaaactca    3360
cgttaaggga ttttggtcat gagattatca aaaaggatct cacctagat ccttttaaat    3420 taaaaatgaa gttttaaatc aatctaaagt atatatgagt aaacttggtc tgacagcggc    3480
cgcaaatgct aaaccactgc agtggttacc aatgcttaat cagtgaggca cctatctcag    3540
cgatctgtct atttcgttca tccatagttg cctgactccc cgtcgtgtag ataactacga    3600
tacgggaggg cttaccatct ggccccagcg ctgcgatgat accgcgagaa ccacgctcac    3660
cggctccgga tttatcagca ataaaccagc cagccggaag ggccgagcgc agaagtggtc    3720
ctgcaacttt atccgcctcc atccagtcta ttaattgttg ccgggaagct agagtaagta    3780
gttcgccagt taatagtttg cgcaacgttg ttgccatcgc tacaggcatc gtggtgtcac    3840
gctcgtcgtt tggtatggct tcattcagct ccggttccca acgatcaagg cgagttacat    3900
gatcccccat gttgtgcaaa aaagcggtta gctccttcgg tcctccgatc gttgtcagaa    3960
gtaagttggc cgcagtgtta tcactcatgg ttatggcagc actgcataat tctcttactg    4020
tcatgccatc cgtaagatgc ttttctgtga ctggtgagta ctcaaccaag tcattctgag    4080
aatagtgtat gcggcgaccg agttgctctt gcccggcgtc aatacgggat aataccgcgc    4140
cacatagcag aactttaaaa gtgctcatca ttggaaaacg ttcttcgggg cgaaaactct    4200
caaggatctt accgctgttg agatccagtt cgatgtaacc cactcgtgca cccaactgat    4260
cttcagcatc ttttactttc accagcgttt ctgggtgagc aaaaacagga aggcaaaatg    4320
ccgcaaaaaa gggaataagg gcgacacgga aatgttgaat actcatactc gtccttttc    4380 aatattattg aagcatttat cagggttact agtacgtctc tcaaggataa gtaagtaata    4440
ttaaggtacg ggaggtattg gacaggccgc aataaaatat ctttattttc attacatctg    4500
tgtgttggtt ttttgtgtga atcgatagta ctaacatacg ctctccatca aaacaaaacg    4560
aaacaaaaca aactagcaaa ataggctgtc cccagtgcaa gtgcaggtgc cagaacattt    4620
ctct                                                                 4624
```

<210> SEQ ID NO 9
<211> LENGTH: 11
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 9
gtgyarttaa t                                                            11

<210> SEQ ID NO 10
<211> LENGTH: 5
<212> TYPE: DNA
<213> ORGANISM: Artificial Sequence

```
<220> FEATURE:
<223> OTHER INFORMATION: transcription factor recognition motif excluded
      from optimized Renilla lucierase with PEST sequence

<400> SEQUENCE: 10 gcgtg                                                                    5

<210> SEQ ID NO 11
<211> LENGTH: 11
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 11
cagccaatga g                                                            11

<210> SEQ ID NO 12
<211> LENGTH: 18
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (15)..(15)
<223> OTHER INFORMATION: n is a, c, g, or t

<400> SEQUENCE: 12
kkrgttattt ttarncmg                                                     18

<210> SEQ ID NO 13
<211> LENGTH: 6
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 13 accaca                                                                   6

<210> SEQ ID NO 14
<211> LENGTH: 8
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 14 ctgastca                                                                 8

<210> SEQ ID NO 15
<211> LENGTH: 9
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (4)..(6)
<223> OTHER INFORMATION: n is a, c, g, or t

<400> SEQUENCE: 15
``` scynnnggc                                                                  9

```
<210> SEQ ID NO 16
<211> LENGTH: 9
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (8)..(8)
<223> OTHER INFORMATION: n is a, c, g, or t

<400> SEQUENCE: 16
``` gcagctgny                                                                  9

```
<210> SEQ ID NO 17
<211> LENGTH: 10
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (9)..(9)
<223> OTHER INFORMATION: n is a, c, g, or t

<400> SEQUENCE: 17
```
wcaggtgwnw                                                                10

```
<210> SEQ ID NO 18
<211> LENGTH: 11
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 18
```
anwcaggtrn r                                                              11

```
<210> SEQ ID NO 19
<211> LENGTH: 11
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 19
```
tgacgtcarr g                                                              11

```
<210> SEQ ID NO 20
<211> LENGTH: 8
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
```

```
<400> SEQUENCE: 20 tgacgtgg                                                                    8

<210> SEQ ID NO 21
<211> LENGTH: 11
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (10)..(10)
<223> OTHER INFORMATION: n is a, c, g, or t

<400> SEQUENCE: 21
srtgagtcan c                                                               11

<210> SEQ ID NO 22
<211> LENGTH: 13
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 22
yknattwysn atg                                                             13

<210> SEQ ID NO 23
<211> LENGTH: 11
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t

<400> SEQUENCE: 23
knttgcnyaa y                                                               11

<210> SEQ ID NO 24
<211> LENGTH: 9
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 24 grggstggg                                                                   9

<210> SEQ ID NO 25
<211> LENGTH: 12
```

```
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 25
gatttaacat aa                                                           12

<210> SEQ ID NO 26
<211> LENGTH: 12
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 26
rntaatcgat nw                                                           12

<210> SEQ ID NO 27
<211> LENGTH: 14
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 27
ggymataaaa ntnt                                                         14

<210> SEQ ID NO 28
<211> LENGTH: 11
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 28
rtgcaatmcc c                                                            11

<210> SEQ ID NO 29
<211> LENGTH: 8
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 29 gctaatta                                                                 8
```

```
<210> SEQ ID NO 30
<211> LENGTH: 15
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t

<400> SEQUENCE: 30
gctggntngn ncyng                                                    15

<210> SEQ ID NO 31
<211> LENGTH: 9
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 31 scgatcgat                                                            9

<210> SEQ ID NO 32
<211> LENGTH: 5
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 32 tgacg                                                                5

<210> SEQ ID NO 33
<211> LENGTH: 9
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (3)..(4)
<223> OTHER INFORMATION: n is a, c, g, or t

<400> SEQUENCE: 33 ggnnttycc                                                            9

<210> SEQ ID NO 34
<211> LENGTH: 12
<212> TYPE: DNA
```

-continued

<210> SEQ ID NO 34
<211> LENGTH: 12
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (9)..(11)
<223> OTHER INFORMATION: n is a, c, g, or t

<400> SEQUENCE: 34
kgrgattann nr                                                          12

<210> SEQ ID NO 35
<211> LENGTH: 7
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (3)..(3)
<223> OTHER INFORMATION: n is a, c, g, or t

<400> SEQUENCE: 35 gtntgct                                                                 7

<210> SEQ ID NO 36
<211> LENGTH: 8
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 36 gcgcsaaa                                                                8

<210> SEQ ID NO 37
<211> LENGTH: 10
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 37 rttacrtaay                                                             10

<210> SEQ ID NO 38
<211> LENGTH: 10
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 38 gtgacgtars                                                             10

<210> SEQ ID NO 39
<211> LENGTH: 11
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 39

```
gtgggsgcrr s                                                               11

<210> SEQ ID NO 40
<211> LENGTH: 12
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t

<400> SEQUENCE: 40
rnwmnaggaa rt                                                              12

<210> SEQ ID NO 41
<211> LENGTH: 8
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 41 ccggaart                                                                    8

<210> SEQ ID NO 42
<211> LENGTH: 10
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (2)..(4)
<223> OTHER INFORMATION: n is a, c, g, or t

<400> SEQUENCE: 42 rnnntgacct                                                                 10

<210> SEQ ID NO 43
<211> LENGTH: 9
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 43 cacttcctg                                                                   9

<210> SEQ ID NO 44
<211> LENGTH: 11
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (2)..(2)
<223> OTHER INFORMATION: n is a, c, g, or t
```

<400> SEQUENCE: 44
tnygtgttkt g                                                           11

<210> SEQ ID NO 45
<211> LENGTH: 13
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 45
waaayaaaca atm                                                         13

<210> SEQ ID NO 46
<211> LENGTH: 8
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 46 rwaaacaa                                                                8

<210> SEQ ID NO 47
<211> LENGTH: 11
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 47
tgtttattta c                                                           11

<210> SEQ ID NO 48
<211> LENGTH: 15
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (13)..(13)
<223> OTHER INFORMATION: n is a, c, g, or t

<400> SEQUENCE: 48
ctwawgtaaa canwg                                                       15

<210> SEQ ID NO 49
<211> LENGTH: 6
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 49 cggaag                                                                  6

<210> SEQ ID NO 50
<211> LENGTH: 6
<212> TYPE: DNA
<213> ORGANISM: Artificial Sequence

```
<220> FEATURE:
<223> OTHER INFORMATION: transcription factor recognition motif excluded
      from optimized Renilla lucierase with PEST sequence

<400> SEQUENCE: 50 wgatar                                                              6

<210> SEQ ID NO 51
<211> LENGTH: 8
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 51 ccgcacgt                                                            8

<210> SEQ ID NO 52
<211> LENGTH: 14
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (8)..(8)
<223> OTHER INFORMATION: n is a, c, g, or t

<400> SEQUENCE: 52
ggttaatnwt tamc                                                    14

<210> SEQ ID NO 53
<211> LENGTH: 10
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 53 trtttrytyw                                                         10

<210> SEQ ID NO 54
<211> LENGTH: 14
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 54
tgamctttgm mcyt                                                    14

<210> SEQ ID NO 55
<211> LENGTH: 12
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (1)..(1)
<223> OTHER INFORMATION: n is a, c, g, or t

<400> SEQUENCE: 55
```

```
nwaaatcaat aw                                                              12

<210> SEQ ID NO 56
<211> LENGTH: 8
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 56 cyaattwt                                                                    8

<210> SEQ ID NO 57
<211> LENGTH: 12
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 57
ctgttgaawa tt                                                              12

<210> SEQ ID NO 58
<211> LENGTH: 8
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (4)..(5)
<223> OTHER INFORMATION: n is a, c, g, or t

<400> SEQUENCE: 58 gaannttc                                                                    8

<210> SEQ ID NO 59
<211> LENGTH: 12
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 59
cagtttcayt ty                                                              12

<210> SEQ ID NO 60
<211> LENGTH: 12
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (11)..(12)
<223> OTHER INFORMATION: n is a, c, g, or t

<400> SEQUENCE: 60
ggyattccca nn                                                              12

<210> SEQ ID NO 61
<211> LENGTH: 12
<212> TYPE: DNA
```

```
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (9)..(11)
<223> OTHER INFORMATION: n is a, c, g, or t

<400> SEQUENCE: 61
kgtcattann nc                                                            12

<210> SEQ ID NO 62
<211> LENGTH: 15
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 62
nncrstttca nttyy                                                         15

<210> SEQ ID NO 63
<211> LENGTH: 7
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 63 aagtgaa                                                                   7

<210> SEQ ID NO 64
<211> LENGTH: 13
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 64
ggtttcrctt tts                                                           13

<210> SEQ ID NO 65
<211> LENGTH: 15
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (14)..(14)
```

<223> OTHER INFORMATION: n is a, c, g, or t

<400> SEQUENCE: 65
antttcgnwt tcsna                                                                15

<210> SEQ ID NO 66
<211> LENGTH: 7
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 66 awtttcc                                                                          7

<210> SEQ ID NO 67
<211> LENGTH: 6
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 67 ctttga                                                                           6

<210> SEQ ID NO 68
<211> LENGTH: 10
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 68
ttaattaatt                                                                      10

<210> SEQ ID NO 69
<211> LENGTH: 9
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 69 yctcccaaa                                                                        9

<210> SEQ ID NO 70
<211> LENGTH: 8
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 70 ggggaggg                                                                         8

<210> SEQ ID NO 71
<211> LENGTH: 12
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

```
<400> SEQUENCE: 71
ytaaawatag cy                                                         12

<210> SEQ ID NO 72
<211> LENGTH: 6
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 72 tgacag                                                                 6

<210> SEQ ID NO 73
<211> LENGTH: 16
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (14)..(14)
<223> OTHER INFORMATION: n is a, c, g, or t

<400> SEQUENCE: 73
gttgcwwggy aacngs                                                     16

<210> SEQ ID NO 74
<211> LENGTH: 14
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 74
tntgcacncg gccc                                                       14

<210> SEQ ID NO 75
<211> LENGTH: 7
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t

<400> SEQUENCE: 75 gncngtt                                                                7

<210> SEQ ID NO 76
```

```
<211> LENGTH: 6
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 76 cacgtg                                                                     6

<210> SEQ ID NO 77
<211> LENGTH: 8
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (2)..(2)
<223> OTHER INFORMATION: n is a, c, g, or t

<400> SEQUENCE: 77 rncaggtg                                                                   8

<210> SEQ ID NO 78
<211> LENGTH: 8
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (7)..(7)
<223> OTHER INFORMATION: n is a, c, g, or t

<400> SEQUENCE: 78 gtaaktng                                                                   8

<210> SEQ ID NO 79
<211> LENGTH: 14
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (4)..(9)
<223> OTHER INFORMATION: n is a, c, g, or t

<400> SEQUENCE: 79
tggnnnnnng ccaa                                                           14

<210> SEQ ID NO 80
<211> LENGTH: 6
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 80 tggaaa                                                                     6

<210> SEQ ID NO 81
<211> LENGTH: 11
<212> TYPE: DNA
```

```
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 81
rtgactcagc a                                                              11

<210> SEQ ID NO 82
<211> LENGTH: 9
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 82 cggccatct                                                                  9

<210> SEQ ID NO 83
<211> LENGTH: 9
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 83 ysattggyy                                                                  9

<210> SEQ ID NO 84
<211> LENGTH: 8
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 84 cwtaattg                                                                   8

<210> SEQ ID NO 85
<211> LENGTH: 7
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 85 tyaagtg                                                                    7

<210> SEQ ID NO 86
<211> LENGTH: 13
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 86
twtttaattg gtt                                                            13

<210> SEQ ID NO 87
<211> LENGTH: 9
<212> TYPE: DNA
<213> ORGANISM: Artificial Sequence
```

```
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (3)..(3)
<223> OTHER INFORMATION: n is a, c, g, or t

<400> SEQUENCE: 87 wantaawta                                                                  9

<210> SEQ ID NO 88
<211> LENGTH: 10
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 88 ygcgcatgcg                                                                10

<210> SEQ ID NO 89
<211> LENGTH: 21
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 89
ttcagcacca cggacagmgc c                                                   21

<210> SEQ ID NO 90
<211> LENGTH: 10
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (9)..(9)
<223> OTHER INFORMATION: n is a, c, g, or t

<400> SEQUENCE: 90 atgcaaatna                                                                10

<210> SEQ ID NO 91
<211> LENGTH: 19
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 91
cmnnytcyct rgggantng                                                      19
```

<210> SEQ ID NO 92
<211> LENGTH: 11
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (7)..(10)
<223> OTHER INFORMATION: n is a, c, g, or t

<400> SEQUENCE: 92
gggagtnnnn s                                                         11

<210> SEQ ID NO 93
<211> LENGTH: 10
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 93 gggratttcc                                                           10

<210> SEQ ID NO 94
<211> LENGTH: 11
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 94
gtkagttcca g                                                         11

<210> SEQ ID NO 95
<211> LENGTH: 10
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (9)..(9)
<223> OTHER INFORMATION: n is a, c, g, or t

<400> SEQUENCE: 95 aawaattans                                                           10

<210> SEQ ID NO 96
<211> LENGTH: 9
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (8)..(8)
<223> OTHER INFORMATION: n is a, c, g, or t

<400> SEQUENCE: 96 wtgattgnt                                                            9

```
<210> SEQ ID NO 97
<211> LENGTH: 7
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 97 mggawgt                                                               7

<210> SEQ ID NO 98
<211> LENGTH: 11
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (10)..(10)
<223> OTHER INFORMATION: n is a, c, g, or t

<400> SEQUENCE: 98
ytgggattan w                                                         11

<210> SEQ ID NO 99
<211> LENGTH: 10
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 99 atgaataawt                                                           10

<210> SEQ ID NO 100
<211> LENGTH: 10
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 100 attarcataa                                                           10

<210> SEQ ID NO 101
<211> LENGTH: 11
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 101
gcataawtta t                                                         11

<210> SEQ ID NO 102
<211> LENGTH: 14
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (6)..(7)
```

<223> OTHER INFORMATION: n is a, c, g, or t

<400> SEQUENCE: 102
sctgwnnktt tcyc                                                              14

<210> SEQ ID NO 103
<211> LENGTH: 8
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 103 wgaggaag                                                                      8

<210> SEQ ID NO 104
<211> LENGTH: 13
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 104
gttrcywngy nac                                                               13

<210> SEQ ID NO 105
<211> LENGTH: 11
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (8)..(8)
<223> OTHER INFORMATION: n is a, c, g, or t

<400> SEQUENCE: 105
tgacctanwt w                                                                 11

<210> SEQ ID NO 106
<211> LENGTH: 10
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 106
tccagatgtt                                                                   10

<210> SEQ ID NO 107
<211> LENGTH: 14
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

```
<400> SEQUENCE: 107
ggggkkgttt gggg                                                    14

<210> SEQ ID NO 108
<211> LENGTH: 8
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 108 tgrccttg                                                            8

<210> SEQ ID NO 109
<211> LENGTH: 9
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 109 tgtctgtct                                                           9

<210> SEQ ID NO 110
<211> LENGTH: 6
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 110 attgtt                                                              6

<210> SEQ ID NO 111
<211> LENGTH: 10
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 111
ggggcggggc                                                         10

<210> SEQ ID NO 112
<211> LENGTH: 8
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 112 tcacgtga                                                            8

<210> SEQ ID NO 113
<211> LENGTH: 12
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
```

```
<222> LOCATION: (2)..(2)
<223> OTHER INFORMATION: n is a, c, g, or t

<400> SEQUENCE: 113
gnccawataw gg                                                        12

<210> SEQ ID NO 114
<211> LENGTH: 7
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 114 ktwgttt                                                               7

<210> SEQ ID NO 115
<211> LENGTH: 8
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 115 tccmagaa                                                              8

<210> SEQ ID NO 116
<211> LENGTH: 8
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (3)..(3)
<223> OTHER INFORMATION: n is a, c, g, or t

<400> SEQUENCE: 116 canttccs                                                              8

<210> SEQ ID NO 117
<211> LENGTH: 6
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 117 atttcc                                                                6

<210> SEQ ID NO 118
<211> LENGTH: 9
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 118 ttmcgggaa                                                             9

<210> SEQ ID NO 119
<211> LENGTH: 8
```

```
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (2)..(2)
<223> OTHER INFORMATION: n is a, c, g, or t

<400> SEQUENCE: 119 mntgwcct                                                              8

<210> SEQ ID NO 120
<211> LENGTH: 10
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 120 aacagatgkt                                                           10

<210> SEQ ID NO 121
<211> LENGTH: 6
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 121 tataaa                                                                6

<210> SEQ ID NO 122
<211> LENGTH: 8
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 122 gkcrgktt                                                              8

<210> SEQ ID NO 123
<211> LENGTH: 8
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (2)..(3)
<223> OTHER INFORMATION: n is a, c, g, or t

<400> SEQUENCE: 123 wnnatgac                                                              8

<210> SEQ ID NO 124
<211> LENGTH: 8
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
```

```
<400> SEQUENCE: 124 wtcaaags                                                                    8

<210> SEQ ID NO 125
<211> LENGTH: 12
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 125
ttatrtwaac at                                                              12

<210> SEQ ID NO 126
<211> LENGTH: 10
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 126 caggaagtar                                                                 10

<210> SEQ ID NO 127
<211> LENGTH: 9
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 127 rgaggkagg                                                                   9

<210> SEQ ID NO 128
<211> LENGTH: 8
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (6)..(6)
<223> OTHER INFORMATION: n is a, c, g, or t

<400> SEQUENCE: 128 gccatntt                                                                    8

<210> SEQ ID NO 129
<211> LENGTH: 12
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 129
ggctcyatca yc                                                              12

<210> SEQ ID NO 130
<211> LENGTH: 8
<212> TYPE: DNA
<213> ORGANISM: Artificial Sequence
<220> FEATURE:
```

```
<223> OTHER INFORMATION: transcription factor recognition motif excluded
      from optimized Renilla lucierase with PEST sequence

<400> SEQUENCE: 130 gtctagac                                                                   8

<210> SEQ ID NO 131
<211> LENGTH: 13
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (6)..(8)
<223> OTHER INFORMATION: n is a, c, g, or t

<400> SEQUENCE: 131
ggtcannntg acc                                                            13

<210> SEQ ID NO 132
<211> LENGTH: 15
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence
<220> FEATURE:
<221> NAME/KEY: misc_feature
<222> LOCATION: (7)..(9)
<223> OTHER INFORMATION: n is a, c, g, or t

<400> SEQUENCE: 132
agaacannnt gttct                                                          15

<210> SEQ ID NO 133
<211> LENGTH: 12
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 133
ggtcaaaggt ca                                                             12

<210> SEQ ID NO 134
<211> LENGTH: 10
<212> TYPE: DNA
<213> ORGANISM: Artificial Sequence
<220> FEATURE:
<223> OTHER INFORMATION: transcription factor recognition motif excluded
      from optimized Renilla lucierase with PEST sequence

<400> SEQUENCE: 134 rrrcwwgyyy                                                                10

<210> SEQ ID NO 135
<211> LENGTH: 6
<212> TYPE: DNA
<213> ORGANISM: Artificial Sequence
<220> FEATURE:
<223> OTHER INFORMATION: Restriction site excluded from optimized
      Renilla lucierase with PEST sequence

<400> SEQUENCE: 135 acgcgt                                                                     6
```

<210> SEQ ID NO 136
<211> LENGTH: 6
<212> TYPE: DNA
<213> ORGANISM: Artificial Sequence
<220> FEATURE:
<223> OTHER INFORMATION: Restriction site excluded from optimized
      Renilla lucierase with PEST sequence

<400> SEQUENCE: 136 gagctc                                                                     6

<210> SEQ ID NO 137
<211> LENGTH: 6
<212> TYPE: DNA
<213> ORGANISM: Artificial Sequence
<220> FEATURE:
<223> OTHER INFORMATION: Restriction site excluded from optimized
      Renilla lucierase with PEST sequence

<400> SEQUENCE: 137 gctagc                                                                     6

<210> SEQ ID NO 138
<211> LENGTH: 6
<212> TYPE: DNA
<213> ORGANISM: Artificial Sequence
<220> FEATURE:
<223> OTHER INFORMATION: Restriction site excluded from optimized
      Renilla lucierase with PEST sequence

<400> SEQUENCE: 138 ggtacc                                                                     6

<210> SEQ ID NO 139
<211> LENGTH: 6
<212> TYPE: DNA
<213> ORGANISM: Artificial Sequence
<220> FEATURE:
<223> OTHER INFORMATION: Restriction site excluded from optimized
      Renilla lucierase with PEST sequence

<400> SEQUENCE: 139 cctagg                                                                     6

<210> SEQ ID NO 140
<211> LENGTH: 6
<212> TYPE: DNA
<213> ORGANISM: Artificial Sequence
<220> FEATURE:
<223> OTHER INFORMATION: Restriction site excluded from optimized
      Renilla lucierase with PEST sequence

<400> SEQUENCE: 140 tctaga                                                                     6

<210> SEQ ID NO 141
<211> LENGTH: 6
<212> TYPE: DNA
<213> ORGANISM: Artificial Sequence
<220> FEATURE:
<223> OTHER INFORMATION: Restriction site excluded from optimized
      Renilla lucierase with PEST sequence

<400> SEQUENCE: 141 agatct                                                                     6

```
<210> SEQ ID NO 142
<211> LENGTH: 6
<212> TYPE: DNA
<213> ORGANISM: Artificial Sequence
<220> FEATURE:
<223> OTHER INFORMATION: Restriction site excluded from optimized
      Renilla lucierase with PEST sequence

<400> SEQUENCE: 142 aagctt                                                                    6

<210> SEQ ID NO 143
<211> LENGTH: 6
<212> TYPE: DNA
<213> ORGANISM: Artificial Sequence
<220> FEATURE:
<223> OTHER INFORMATION: Restriction site excluded from optimized
      Renilla lucierase with PEST sequence

<400> SEQUENCE: 143 ctcgag                                                                    6

<210> SEQ ID NO 144
<211> LENGTH: 6
<212> TYPE: DNA
<213> ORGANISM: Artificial Sequence
<220> FEATURE:
<223> OTHER INFORMATION: Restriction site excluded from optimized
      Renilla lucierase with PEST sequence

<400> SEQUENCE: 144 cccggg                                                                    6

<210> SEQ ID NO 145
<211> LENGTH: 8
<212> TYPE: DNA
<213> ORGANISM: Artificial Sequence
<220> FEATURE:
<223> OTHER INFORMATION: Restriction site excluded from optimized
      Renilla lucierase with PEST sequence

<400> SEQUENCE: 145 ggccggcc                                                                  8

<210> SEQ ID NO 146
<211> LENGTH: 6
<212> TYPE: DNA
<213> ORGANISM: Artificial Sequence
<220> FEATURE:
<223> OTHER INFORMATION: Restriction site excluded from optimized
      Renilla lucierase with PEST sequence

<400> SEQUENCE: 146 cctagg                                                                    6

<210> SEQ ID NO 147
<211> LENGTH: 6
<212> TYPE: DNA
<213> ORGANISM: Artificial Sequence
<220> FEATURE:
<223> OTHER INFORMATION: Restriction site excluded from optimized
      Renilla lucierase with PEST sequence

<400> SEQUENCE: 147 gtcgac                                                                    6
```

```
<210> SEQ ID NO 148
<211> LENGTH: 6
<212> TYPE: DNA
<213> ORGANISM: Artificial Sequence
<220> FEATURE:
<223> OTHER INFORMATION: Restriction site excluded from optimized
      Renilla lucierase with PEST sequence

<400> SEQUENCE: 148 gaattc                                                                      6

<210> SEQ ID NO 149
<211> LENGTH: 6
<212> TYPE: DNA
<213> ORGANISM: Artificial Sequence
<220> FEATURE:
<223> OTHER INFORMATION: Restriction site excluded from optimized
      Renilla lucierase with PEST sequence

<400> SEQUENCE: 149 ggatcc                                                                      6

<210> SEQ ID NO 150
<211> LENGTH: 274
<212> TYPE: DNA
<213> ORGANISM: Artificial Sequence
<220> FEATURE:
<223> OTHER INFORMATION: Strong constitutive eukaryotic promoter

<400> SEQUENCE: 150
gtacccggtc acctctctga tctgcgcatg tgctgggcta cgcgcgggcg caagcgccaa          60
gagcggctgc gtctatggtc atgacgtctg acagagcgtc cacccgtctt cgacaggact         120
ctatggttct tacgcgcgca gacagaccgc ctatataagc catgcgcagg cggaggagcg         180
cctcttttcc ttcggtgtgg ggagcaagcg cagttgtcgt ctcttgcggt gccgtcgctg         240
gttctcacac cttttaggtc tgttctcgtc ttcc                                     274

<210> SEQ ID NO 151
<211> LENGTH: 1044
<212> TYPE: DNA
<213> ORGANISM: Artificial Sequence
<220> FEATURE:
<223> OTHER INFORMATION: Strong constitutive eukaryotic promoter with
      multiple cloning site for 5'UTR sequences

<400> SEQUENCE: 151
atagcagaca tacaacggac ggtgggccca gacccaggct gtgtagaccc agccccccg           60 ccccgcagtg cctaggtcac ccactaacgc cccaggcctt gtcttggctg ggcgtgactg         120
ttaccctcaa aagcaggcag ctccagggta aaaggtgccc tgccctgtag agcccacctt        180
ccttcccagg gctgcggctg gtaggtttg tagccttcat cacgggccac ctccagccac         240
tggaccgctg gcccctgccc tgtcctgggg agtgtggtcc tgcgacttct aagtggccgc        300
aagccacctg actcccccaa caccacactc tacctctcaa gcccaggtct ctccctagtg        360
acccacccag cacatttagc tagctgagcc ccacagccag aggtcctcag gccctgcttt        420
cagggcagtt gctctgaagt cggcaagggg gagtgactgc ctggccactc catgccctcc        480
aagagctcct tctgcaggag cgtacagaac ccagggccct ggcacccgtg cagaccctgg        540
cccaccccac ctgggcgctc agtgcccaag agatgtccac acctaggatg tccgcggtg         600 ggtgggggc ccgagagacg ggcaggccgg ggcaggcct ggccatgcgg ggccgaaccg           660
ggcactgccc agcgtggggc gcgggggcca cggcgcgcgc cccagccccc cgggcccagc        720
```

```
accccaaggc ggccaacgcc aaaactctcc ctcctcctct tcctcaatct cgctctcgct    780
cttttttttt ttcgcaaaag gaggggagag ggggtaaaaa aatgctgcac tgtgcggcga    840
agccggtgag tgagcggcgc ggggccaatc agcgtgcgcc gttccgaaag ttgccttta    900 tggctcgagc ggccgcggcg cgcccctata aacccagcg gcgcgacgcg ccaccaccgc    960
cgagaccgcg tccgccccga gatctcagag cctcgccttt cttaagccga tccgccggac   1020
gtccacaccc cctgcaggct cacc                                          1044

<210> SEQ ID NO 152
<211> LENGTH: 1059
<212> TYPE: DNA
<213> ORGANISM: Artificial Sequence
<220> FEATURE:
<223> OTHER INFORMATION: Humanized Renilla luciferase with PEST sequence

<400> SEQUENCE: 152
atggcttcca aggtgtacga ccccgagcaa cgcaaacgca tgatcactgg gcctcagtgg     60
tgggctcgct gcaagcaaat gaacgtgctg gactccttca tcaactacta tgattccgag    120
aagcacgccg agaacgccgt gattttctg catggtaacg ctgcctccag ctacctgtgg    180
aggcacgtcg tgcctcacat cgagcccgtg gctagatgca tcatccctga tctgatcgga    240
atgggtaagt ccggcaagag cgggaatggc tcatatcgcc tcctggatca ctacaagtac    300
ctcaccgctt ggttcgagct gctgaacctt ccaaagaaaa tcatctttgt gggccacgac    360
tggggggctt gtctggcctt tcactactcc tacgagcacc aagacaagat caaggccatc    420
gtccatgctg agagtgtcgt ggacgtgatc gagtcctggg acgagtggcc tgacatcgag    480
gaggatatcg ccctgatcaa gagcgaagag ggcgagaaaa tggtgcttga gaataacttc    540
ttcgtcgaga ccatgctccc aagcaagatc atgcggaaac tggagcctga ggagttcgct    600
gcctacctgg agccattcaa ggagaagggc gaggttagac ggcctaccct ctcctggcct    660
cgcgagatcc ctctcgttaa gggaggcaag cccgacgtcg tccagattgt ccgcaactac    720
aacgcctacc ttcgggccag cgacgatctg cctaagatgt tcatcgagtc cgaccctggg    780
ttcttttcca acgctattgt cgaggagct aagaagttcc ctaacaccga gttcgtgaag    840
gtgaagggcc tccacttcag ccaggaggac gctccagatg aaatgggtaa gtacatcaag    900
agcttcgtgg agcgcgtgct gaagaacgag cagaattctc acggcttccc tcccgaggtg    960
gaggagcagg ccgccggcac cctgcccatg agctgcgccc aggagagcgg catggataga   1020
caccctgctg cttgcgccag cgccaggatc aacgtctaa                          1059

<210> SEQ ID NO 153
<211> LENGTH: 936
<212> TYPE: DNA
<213> ORGANISM: Artificial Sequence
<220> FEATURE:
<223> OTHER INFORMATION: Humanized Renilla luciferase

<400> SEQUENCE: 153
atggcttcca aggtgtacga ccccgagcaa cgcaaacgca tgatcactgg gcctcagtgg     60
tgggctcgct gcaagcaaat gaacgtgctg gactccttca tcaactacta tgattccgag    120
aagcacgccg agaacgccgt gattttctg catggtaacg ctgcctccag ctacctgtgg    180
aggcacgtcg tgcctcacat cgagcccgtg gctagatgca tcatccctga tctgatcgga    240
atgggtaagt ccggcaagag cgggaatggc tcatatcgcc tcctggatca ctacaagtac    300
```

-continued

```
ctcaccgctt ggttcgagct gctgaacctt ccaaagaaaa tcatctttgt gggccacgac    360 tgggggctt  gtctggcctt tcactactcc tacgagcacc aagacaagat caaggccatc    420
gtccatgctg agagtgtcgt ggacgtgatc gagtcctggg acgagtggcc tgacatcgag    480
gaggatatcg ccctgatcaa gagcgaagag ggcgagaaaa tggtgcttga gaataacttc    540
ttcgtcgaga ccatgctccc aagcaagatc atgcggaaac tggagcctga ggagttcgct    600
gcctacctgg agccattcaa ggagaagggc gaggttagac ggcctaccct ctcctggcct    660
cgcgagatcc ctctcgttaa gggaggcaag cccgacgtcg tccagattgt ccgcaactac    720
aacgcctacc ttcgggccag cgacgatctg cctaagatgt tcatcgagtc cgaccctggg    780
ttcttttcca acgctattgt cgagggagct aagaagttcc ctaacaccga gttcgtgaag    840
gtgaagggcc tccacttcag ccaggaggac gctccagatg aaatgggtaa gtacatcaag    900
agcttcgtgg agcgcgtgct gaagaacgag cagtaa                              936
```

MODIFIED RENILLA LUCIFERASE NUCLEIC ACIDS AND METHODS OF USE

CROSS-REFERENCE

This application claims the benefit of the priority date of U.S. application 61/397,340, filed Jun. 10, 2010, the contents of which are incorporated herein by reference.

BACKGROUND OF THE INVENTION

Reporter genes are important tools that enable researchers to study DNA sequences that regulate gene expression. Light emitting proteins, such as luciferases, are useful reporter genes since the amount of protein produced can be measured as light output. Luciferase genes have been isolated from a variety of organisms such as insects and a variety of marine organisms. The luciferase gene from the sea pansy (*Renilla reniformis*) is a widely used luciferase reporter and is commonly referred to as "*Renilla*".

Marine luciferases have become popular alternatives to firefly luciferase as a genetic reporter based on assay simplicity, high sensitivity, and a broad linear range of signal that provides greater sensitivity over firefly luciferases. The *Renilla* luciferase protein catalyzes oxidation of its coelenterazine substrate in the reaction shown below to produce light at 480 nm, easily read by standard luminometers. U.S. Pat. No. 5,418,155 (CORMIER, M. J. et al., May 23, 1995) provides an amino acid sequence of *Renilla* luciferase and a nucleotide sequence encoding it. U.S. patent application 2006/0068395 (WOOD, K. V. et al., Mar. 30, 2006) provides another nucleotide sequence encoding *Renilla* luciferase.

SUMMARY OF THE INVENTION

In one aspect this invention provides an isolated nucleic acid molecule comprising a reporter nucleotide sequence encoding a polypeptide comprising a *Renilla* luciferase amino acid sequence (SEQ ID NO: 1), wherein the *Renilla* luciferase amino acid sequence is encoded by a luciferase nucleotide sequence having at least 90% sequence identity with SEQ ID NO: 2. In one embodiment the luciferase nucleotide sequence has at least 95%, at least 98%, at least 99% or at least 99.9% sequence identity with SEQ ID NO: 2. In another embodiment the luciferase nucleotide sequence is SEQ ID NO: 2. In another embodiment the polypeptide is *Renilla* luciferase (SEQ ID NO: 1) (RenS). In another embodiment the luciferase nucleotide sequence is SEQ ID NO: 2. the polypeptide is a fusion protein comprising the *Renilla* luciferase. In another embodiment the luciferase nucleotide sequence is SEQ ID NO: 2. In another embodiment the fusion protein is RenSP (SEQ ID NO: 3). In another embodiment the reporter nucleotide sequence is SEQ ID NO: 4. In another embodiment the polypeptide comprises a protein destabilization domain that decreases the half-life of the luciferase protein. In another embodiment the luciferase nucleotide sequence contains no more than 10, no more than 5, no more than 4, no more than 3, no more than 2, no more than 1 or no regulatory motifs selected from the motifs of FIG. 3. In another embodiment the luciferase nucleotide sequence, when operably linked to a human RPL10 promoter in an expression plasmid, transfected into HT1080 cells and incubated for 30 minutes with a luciferase substrate, expresses at least 10% more signal than hRluc under the same conditions.

In another aspect this invention provides a recombinant nucleic acid comprising a reporter nucleotide sequence encoding a polypeptide comprising a *Renilla* luciferase amino acid sequence (SEQ ID NO: 1), wherein the *Renilla* luciferase amino acid sequence is encoded by a luciferase nucleotide sequence having at least 90% sequence identity with SEQ ID NO: 2. In one embodiment the recombinant nucleic acid comprises an expression control sequence operably linked with the nucleotide sequence. In another embodiment the expression control sequence comprises a mammalian promoter. In another embodiment the expression control sequence comprises a human promoter. In another embodiment the recombinant nucleic acid is contained in a vector is selected from a plasmid vector, a viral vector, a cosmid, a transposon and an artificial chromosome. In another embodiment the recombinant nucleic acid of comprises a cloning site positioned relative to the nucleotide sequence such that an expression control sequence inserted into the cloning site becomes operably linked with the luciferase-encoding nucleotide sequence. In another embodiment the cloning site comprises a plurality of restriction sites. In another embodiment the cloning site is positioned to place a promoter in operable linkage with the luciferase-encoding nucleotide sequence. In another embodiment the cloning site is positioned to place a 5' UTR or a 3'UTR in operable linkage with the luciferase-encoding nucleotide sequence. In another embodiment the recombinant nucleic acid further comprises a promoter operably linked with the luciferase-encoding nucleotide sequence. In another embodiment the promoter is a promoter of the RPL10 gene. In another embodiment the vector is a plasmid comprising an origin or replication, a selectable marker, an origin of replication and a polyA sequence operatively linked with the nucleotide sequence.

In another aspect this invention provides a vector comprising a recombinant nucleic acid comprising a reporter nucleotide sequence encoding a polypeptide comprising a *Renilla* luciferase amino acid sequence (SEQ ID NO: 1), wherein the *Renilla* luciferase amino acid sequence is encoded by a luciferase nucleotide sequence having at least 90% sequence identity with SEQ ID NO: 2.

In another aspect this invention provides a recombinant cell comprising a recombinant nucleic acid comprising a reporter nucleotide sequence encoding a polypeptide comprising a *Renilla* luciferase amino acid sequence (SEQ ID NO: 1), wherein the *Renilla* luciferase amino acid sequence is encoded by a luciferase nucleotide sequence having at least 90% sequence identity with SEQ ID NO: 2. In one embodiment the recombinant nucleic acid comprises an expression control sequence operably linked with the nucleotide sequence. In another embodiment the recombinant nucleic acid is contained in a vector is selected from a plasmid vector, a viral vector, a cosmid, a transposon and an artificial chromosome. In another embodiment the recombinant cell is a mammalian cell, e.g. a human cell. In another embodiment the expression construct is stably integrated in the genome of the host cell. In another embodiment the recombinant nucleic acid is maintained in the cell as a stable episomal vector. In another embodiment the recombinant nucleic acid is integrated into the genome of the host cell.

In another aspect this invention provides a kit comprising a vector comprising a recombinant nucleic acid comprising a reporter nucleotide sequence encoding a polypeptide comprising a *Renilla* luciferase amino acid sequence (SEQ ID NO: 1), wherein the *Renilla* luciferase amino acid sequence is encoded by a luciferase nucleotide sequence having at least 90% sequence identity with SEQ ID NO: 2 and a luciferase substrate.

In another aspect this invention provides a device comprising a plurality of receptacles, wherein each receptacle comprises a vector comprising a recombinant nucleic acid comprising a reporter nucleotide sequence encoding a polypeptide comprising a *Renilla* luciferase amino acid sequence (SEQ ID NO: 1), wherein the *Renilla* luciferase amino acid sequence is encoded by a luciferase nucleotide sequence having at least 90% sequence identity with SEQ ID NO: 2. In one embodiment a plurality of the expression constructs comprises a different promoter. In another embodiment the plurality of the expression constructs comprises the same promoter.

In another aspect this invention provides a method comprising measuring a signal produced by a recombinant cell comprising an expression construct comprising an expression control sequence operably linked with the nucleotide sequence encoding a polypeptide comprising a *Renilla* luciferase amino acid sequence (SEQ ID NO: 1), wherein the *Renilla* luciferase amino acid sequence is encoded by a luciferase nucleotide sequence having at least 90% sequence identity with SEQ ID NO: 2.

In another aspect this invention provides a method of screening a test condition for its effect on expression of a reporter polypeptide comprising: a) exposing a recombinant cell comprising an expression construct comprising an expression control sequence operably linked with the nucleotide sequence encoding a polypeptide comprising a *Renilla* luciferase amino acid sequence (SEQ ID NO: 1), wherein the *Renilla* luciferase amino acid sequence is encoded by a luciferase nucleotide sequence having at least 90% sequence identity with SEQ ID NO: 2 to a test condition; b) measuring expression of the polypeptide; and c) comparing the measurement with a measurement of expression of the cell not exposed to the test condition. In one embodiment the test condition is selected from the group consisting of contacting the cell with a test compound, exposing the cell to an environmental condition and inducing or repressing expression of one or more genes in the cell. In one embodiment the test condition comprises contacting the cell with a test compound selected from: (1) a small organic molecule; (2) a nucleic acid derivative (e.g., a small interfering RNA, micro RNA mimic or micro RNA inhibitor); and (3) an expression construct that contains an open reading frame of a gene.

In another aspect this invention provides a method comprising: a) exposing a plurality of recombinant cells comprising an expression construct comprising an expression control sequence operably linked with the nucleotide sequence encoding a polypeptide comprising a *Renilla* luciferase amino acid sequence (SEQ ID NO: 1), wherein the *Renilla* luciferase amino acid sequence is encoded by a luciferase nucleotide sequence having at least 90% sequence identity with SEQ ID NO: 2 to a test condition; and b) measuring expression of the polypeptide in the cells. In one embodiment the method further comprises: c) comparing the measurements. In another embodiment the cells are exposed to a test condition.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

FIG. 3 provides nucleotide and amino acid sequences.

DETAILED DESCRIPTION OF THE INVENTION

Figure 1:
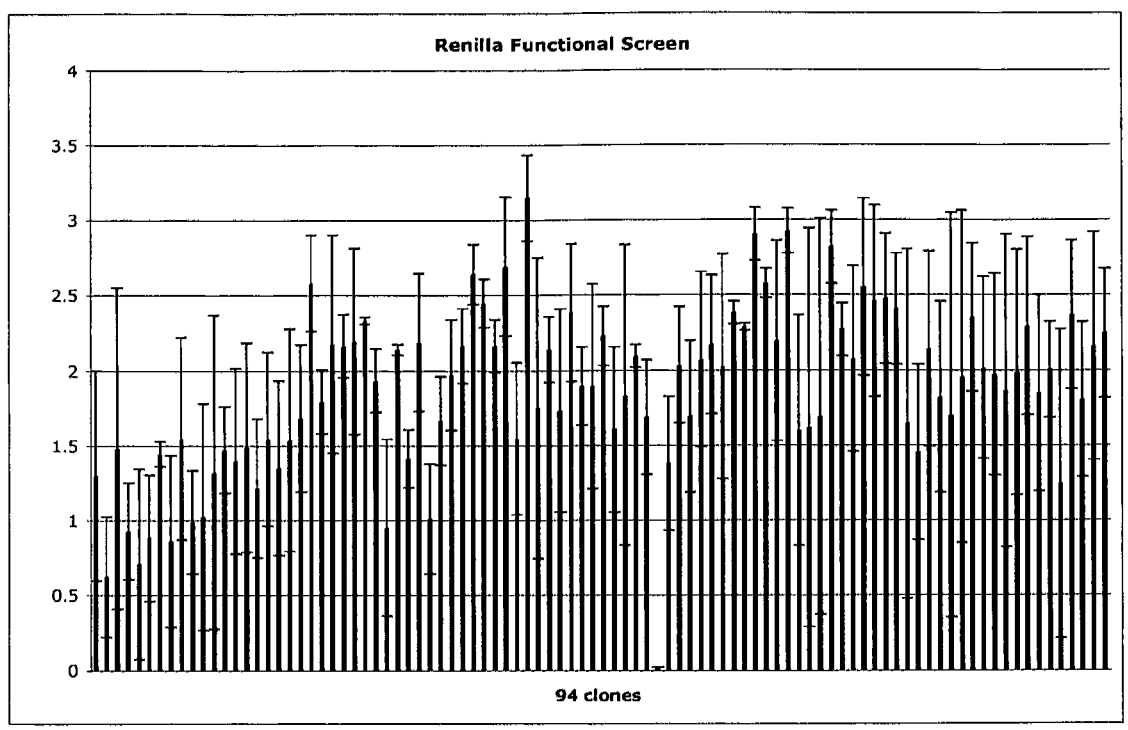
FIG. 1 shows results from the functional screen of *Renilla* codon variants.
Figure 2:
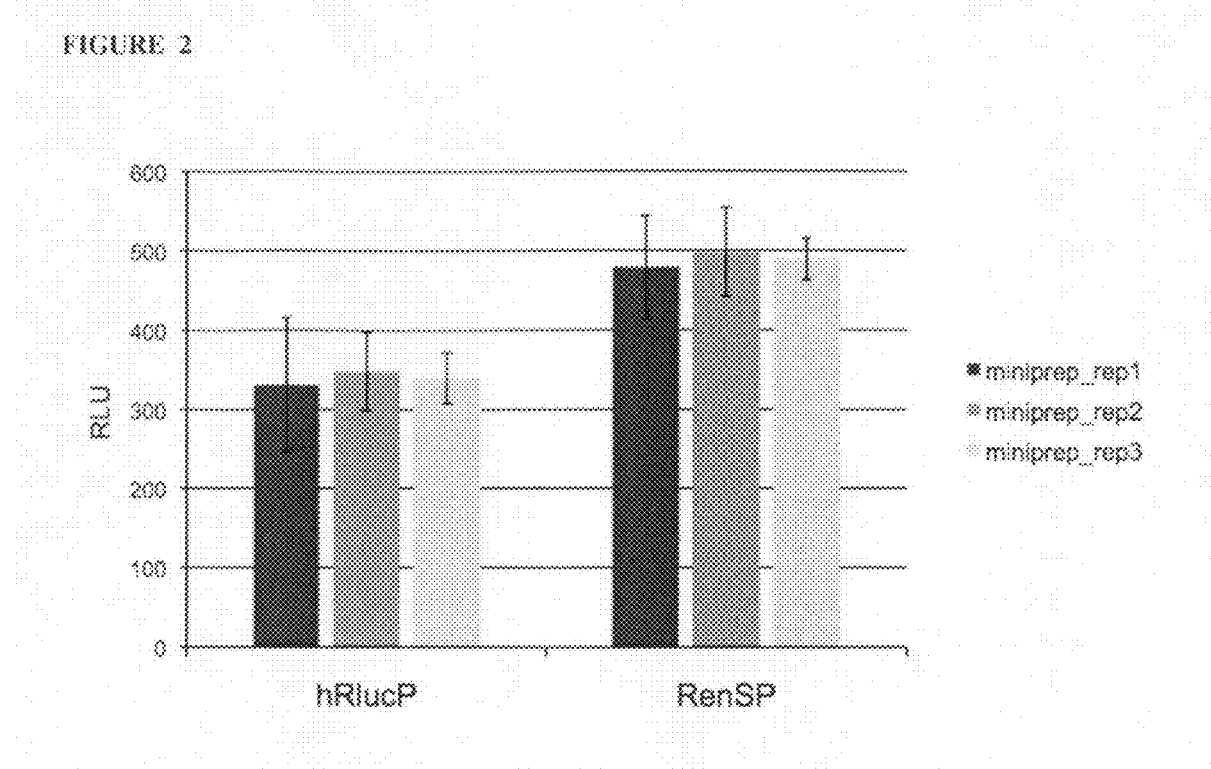
FIG. 2 shows differences in expression of wild type luciferase and the luciferase of SEQ ID NO: 2.

It is desirable to maximize the expression of a reporter protein to maximize signal. One approach to maximize expression is to optimize the codon usage of a reporter gene to maximize the translation rate in an organism other than the native organism from which the gene was isolated. Furthermore, it is desirable to remove potential regulatory sequences from the gene itself that may confound measurements of other regulatory elements of interest. There are many different approaches for optimizing the expression of a reporter gene. In the present invention, we identified a novel and improved nucleotide sequence for *Renilla* by screening hundreds of codon variants of a cDNA coding for the *Renilla* protein in human cells and eliminated many putative transcription factor binding sites from the nucleotide sequence as well.

1. Nucleotide Sequences Encoding Luciferase

This invention provides nucleotide sequences encoding luciferase. The nucleotide sequence can encode a *Renilla* luciferase having the amino acid sequence of SEQ ID NO: 1 (RenS), or an amino acid sequence having at least 90%, at least 95%, or at least 99% sequence identity with SEQ ID NO: 1. Such amino acid sequences are referred to herein as "luciferase polypeptides". A nucleotide sequence encoding a luciferase polypeptide is referred to herein as a "luciferase nucleotide sequence." The nucleotide sequence encoding a luciferase polypeptide can have the nucleotide sequence of SEQ ID NO: 2 or it can have at least 90%, at least 95%, at least 98%, at least 99%, at least 99.5%, at least 99.6%, at least 99.7%, at least 99.8% or at least 99.9% sequence identity with SEQ ID NO: 2. Alternatively, a nucleic acid having a nucleotide sequence encoding a luciferase polypeptide can hybridize under stringent conditions to a nucleic acid of SEQ ID NO: 2.

Nucleotide sequences that are different from SEQ ID NO: 2 and that encode SEQ ID NO: 1 can be generated by choosing an alternative codon consistent with the genetic code for one that encodes a particular amino acid in the amino acid sequence on luciferase. Accordingly, generating nucleotide sequences encoding the luciferase polypeptide and having a selected level of sequence homology with SEQ ID NO: 2 is a straightforward matter.

Nucleic acids can be made by any methods known in the art. This includes the use of nucleic acid synthesizers, or commercially available services, such as DNA2.0 (Menlo Park, Calif.).

The luciferase sequences of this invention express enzymatically active protein at higher levels than wild type *Renilla* luciferase genes. More specifically, the nucleotide sequences of this invention exhibit at least 10%, at least 15%, at least 20%, at least 50%, at least 75% or at least 100% greater expression than hRluc. hRluc is a humanized luciferase gene disclosed in U.S. patent application 2006/0068395 (WOOD, K. V. et al., Mar. 30, 2006). It is presented here has SEQ ID NO: 153, and with a PEST sequence attached as SEQ ID NO: 152. Relative expression can be determined in the following assay. hRlucP (SEQ ID NO: 153) and a luciferase gene to be tested are cloned into a vector, such as pLightSwitch prom (SEQ ID NO:5) (available from SwitchGear Genomics, Menlo Park, Calif.) operably linked with a human RPL10 promoter. 50 ng of each plasmid is transfected with FuGENE HD into human HT1080 cells. After 24 hours of incubation, 100 uL of LightSwitch Reagent (SwitchGear Genomics) is added to each well and incubated for 30 minutes. Expression is measured as a function of light emitted (read for 2 seconds on an LmaxII-384 luminometer). Alternatively, the assay can use luciferase genes with PEST sequence attached.

The nucleotide sequence of SEQ ID NO: 2 does not include any of the regulatory motifs of SEQ ID NOs: 9-134. The nucleotide sequences of this invention that are not identical to SEQ ID NO: 2 can have, for example, at most one, at most two, at most three, at most four, at most five or at most 10% of the sequence motifs of SEQ ID NOs: 9-134.

The nucleotide sequence of SEQ ID NO: 2 also does not have any of the restriction sites of SEQ ID NOs: 135-149. The nucleotide sequences of this invention that are not identical to SEQ ID NO: 2 can have, for example, at most one, at most two, at most three, at most four or at most five of the restriction sites of SEQ ID NOs: 9-134.

This invention also provides nucleotide sequences encoding a luciferase fusion protein. In such fusion proteins a luciferase polypeptide is attached at its amino terminus or its carboxy terminus to another amino acid sequence. A polypeptide comprising a luciferase polypeptide amino acid sequence is referred to herein as a "reporter polypeptide". A nucleotide sequence encoding a reporter polypeptide is referred to herein as a "reporter nucleotide sequence." Luciferase polypeptides and luciferase nucleotide sequences are, themselves, examples of reporter polypeptides and reporter nucleotide sequences, respectively.

In one embodiment the luciferase fusion protein comprises luciferase having a protein destabilization domain. For example, the protein destabilization domain can be a PEST sequence attached at the carboxy terminus of luciferase. Such an amino acid sequence is RenSP, provided as SEQ ID NO: 3. A nucleotide sequence encoding this amino acid sequence is provided as SEQ ID NO: 4.

In another embodiment the luciferase fusion protein comprises a gene-encoded polypeptide tagged with luciferase. Typically, luciferase is attached at the carboxy terminus of the polypeptide. The nucleotide sequences encoding such proteins are useful, for example, in understanding the regulation of a gene in its native genomic context.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

A "reference sequence" is a defined sequence used as a basis for a sequence comparison and may be a subset of a larger sequence, e.g., a complete cDNA, protein, or gene sequence.

Because two polynucleotides or polypeptides each may comprise (1) a sequence (i.e., only a portion of the complete polynucleotide or polypeptide sequence) that is similar between the two polynucleotides, or (2) a sequence that is divergent between the two polynucleotides, sequence comparisons between two (or more) polynucleotides or polypeptides are typically performed by comparing sequences of the two polynucleotides over a "comparison window" to identify and compare local regions of sequence similarity.

A "comparison window" refers to a conceptual segment of typically at least 12 consecutive nucleotides or 4 consecutive amino acid residues that is compared to a reference sequence. The comparison window frequently has a length of at least 15 or at least 25 nucleotides or at least 5 or at least 8 amino acids. The comparison window may comprise additions or deletions (i.e., gaps) of about 20 percent or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Dr., Madison, Wis.) or by inspection, and the best alignment (i.e., resulting in the highest percentage of similarity over the comparison window) generated by any of the various methods is selected.

A subject nucleotide sequence or amino acid sequence is "identical" to a reference sequence if the two sequences are the same when aligned for maximum correspondence over the length of the nucleotide or amino acid sequence.

The "percentage of sequence identity" between two sequences is calculated by comparing two optimally aligned sequences over a comparison window, determining the number of positions at which the identical nucleotide or amino acid occurs in both sequences to yield the number of matched positions, dividing the number of matched positions by the total number of positions in the window of comparison (i.e., the window size), and multiplying the result by 100 to yield the percentage of sequence identity.

Unless otherwise specified, the comparison window used to compare two sequences is the length of the shorter sequence.

Methods are described further in Natl. Acad. Sci. USA 85:2444; Higgins & Sharp (1988) Gene 73:237-244; Higgins & Sharp, CABIOS 5:151-153 (1989); Corpet et al. (1988) Nucleic Acids Research 16:10881-90; Huang et al. (1992) Computer Applications in the Biosciences 8:155-65; and Pearson et al. (1994) Methods in Molecular Biology 24:307-31. Alignment is also often performed by inspection and manual alignment.

A subject nucleotide sequence or amino acid sequence is "substantially identical" to a reference sequence if the subject amino acid sequence or nucleotide sequence has at least 70% sequence identity over a comparison window. Thus, sequences that have at least 70%, at least 80% sequence identity, at least 85% sequence identity, at least 90% sequence identity, at least 95% sequence identity, at least 98% sequence identity or at least 99% sequence identity with the reference sequence are also "substantially identical. Two sequences that are identical to each other are, of course, also "substantially identical".

"Hybridizing specifically to" or "specific hybridization" or "selectively hybridize to", refers to the binding, duplexing, or hybridizing of a nucleic acid molecule preferentially to a particular nucleotide sequence under stringent conditions when that sequence is present in a complex mixture (e.g., total cellular) DNA or RNA.

The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) Laboratory Techniques in Biochemistry and Molecular Biology—Hybridization with Nucleic Acid Probes part I chapter 2 "Overview of principles of hybridization and the strategy of nucleic acid probe assays", Elsevier, New York.

Generally, highly stringent hybridization and wash conditions are selected to be about 5° C. lower than thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, Sambrook et al. for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. In general, a signal to noise ratio of 2× (or higher) than that observed for an unrelated probe in the particular hybridization assay indicates detection of a specific hybridization.

In certain embodiments, the nucleic acids of this invention are isolated nucleic acids. "Substantially pure" or "isolated" means an object species is the predominant species present (i.e., on a molar basis, more abundant than any other individual macromolecular species in the composition), and a substantially purified fraction is a composition wherein the object species comprises at least about 50% (on a molar basis) of all macromolecular species present. Generally, a substantially pure composition means that about 80% to 90% or more of the macromolecular species present in the composition is the purified species of interest. The object species is purified to essential homogeneity (contaminant species cannot be detected in the composition by conventional detection methods) if the composition consists essentially of a single macromolecular species. Solvent species, small molecules (<500 Daltons), stabilizers (e.g., BSA), and elemental ion species are not considered macromolecular species for purposes of this definition.

The luciferase-encoding nucleic acids of this invention are not naturally occurring. "Naturally occurring" as applied to an object refers to the fact that the object can be found in nature. For example, a polypeptide or polynucleotide sequence that is present in an organism (including viruses) that can be isolated from a source in nature and which has not been intentionally modified by man in the laboratory is naturally-occurring.

2. Recombinant Nucleic Acid Molecules 2.1 Expression Constructs

An expression construct is a recombinant polynucleotide comprising expression control sequences operably linked to a nucleotide sequence to be expressed. Expression constructs typically include sufficient cis-acting elements for expression. Other elements for expression can be supplied by the host cell or in vitro expression system.

This invention also provides recombinant nucleic acid molecules in which a nucleotide sequence encoding a luciferase or a luciferase fusion protein is linked with other functional nucleotide sequences. Recombinant nucleic acid molecules, also referred to as recombinant polynucleotides, are polynucleotides having sequences that are not naturally joined together.

In particular, this invention provides recombinant nucleic acid molecules in which a nucleotide sequence of this invention is operably linked with an expression control sequence. A recombinant nucleic acid molecule comprising an expression control sequence operably linked with a nucleotide sequence encoding a polypeptide is referred to herein as an expression construct. The expression control sequence can be positioned upstream or downstream of the luciferase-encoding nucleotide sequence.

2.2 Expression Control Sequences

An expression control sequence is a nucleotide sequence in a polynucleotide that regulates the expression (transcription and/or translation) of a nucleotide sequence operably linked to it. "Operably linked" refers to a functional relationship between two parts in which the activity of one part (e.g., the ability to regulate transcription) results in an action on the other part (e.g., transcription of the sequence). Expression control sequences include, for example, promoters (e.g., inducible or constitutive), enhancers, transcription terminators and splicing signals for introns.

2.2.1 Promoters

Promoters are the best-characterized transcriptional regulatory sequences because of their predictable location immediately upstream of transcription start sites. Promoters include sequences that modulate the recognition, binding and transcription initiation activity of the RNA polymerase. These sequences can be cis acting or can be responsive to trans acting factors. Promoters, depending upon the nature of the regulation, can be constitutive or regulated. They are often described as having two separate segments: core and extended promoter regions.

The core promoter includes sequences that are sufficient for RNA polymerase recognition, binding and transcription initiation. The core promoter includes the transcriptional start site, an RNA polymerase binding site and other general transcription binding sites and is where the pre-initiation complex forms and the general transcription machinery assembles. It is generally within 50 nucleotides (nt) of the transcription start site (TSS).

The extended promoter region includes the so-called proximal promoter, which extends to about 250 nucleotides upstream of the transcriptional start site (i.e., −250 nt). It includes primary regulatory elements such as specific transcription factor binding sites. It has been found that many genes have transcription regulatory elements located further up-stream. In particular, a fragment that includes most of the transcription regulatory elements of a gene can extend up to 700 nt or more up-stream of the transcription start site. (See, e.g., U.S. 2007-0161031.) In certain genes, transcription regulatory sequences have been found thousands of nucleotides upstream of the transcriptional start site.

Any promoter of interest can be operably linked with a luciferase-encoding nucleotide sequence. For example, the promoter can be a constitutive promoter. Alternatively, the promoter can be inducible promoter. This invention contemplates the choice of any promoter of interest to the artisan. A variety of promoters are commercially available from Switchgear Genomics (www.switchgeargenomics.com) and also are described in U.S. patent publications U.S. 2007-0161031 (Jul. 12, 2007, TRINKLEIN, N. D. et al.), U.S. 2009-0018031 (Jan. 15, 2009, TRINKLEIN, N. D. et al.) and U.S. 2011-0065100 (Mar. 17, 2011, ALDRED, S. F. et al.).

2.2.2 Other Transcription Regulatory Sequences

Transcription regulatory sequences include nucleotide sequences that confer inducible expression of a gene (i.e., that require a substance or stimulus for increased transcription). When an inducer is present, or present at increased concentration, gene expression increases. Regulatory regions also include sequences that confer repression of gene expression (i.e., a substance or stimulus decreases transcription). When a repressor is present or at increased concentration, gene expression decreases. Regulatory regions typically bind one or more trans-acting or cis-acting proteins. Enhancers are known to influence gene expression when positioned 5' or 3' of the gene, or when positioned in or a part of an exon or an intron. Enhancers also can function at a significant distance from the gene, for example, at a distance from about 3 Kb, 5 Kb, 7 Kb, 10 Kb, 15 Kb or more.

Regulatory regions also include, in addition to transcription regulatory sequences, sequences in DNA or RNA molecules that regulate transcript stability, transcript localization, facilitate translation, splicing signals for introns, maintenance of the correct reading frame of the gene to permit in-frame translation of mRNA and, stop codons, leader sequences and fusion partner sequences, internal ribosome binding sites (IRES) elements for the creation of multigene, or polycistronic, messages, polyadenylation signals to provide proper polyadenylation of the transcript of a gene of interest and stop codons and can be optionally included in an expression vector.

The expression control sequence can be a 5'- or a 3'-untranslated region (UTR) of a messenger RNA. Such UTRs also are commercially available from Switchgear Genomics and are described in U.S. patent publication U.S. 2008-0220983 (Sep. 11, 2008, TRINKLEIN, N. D. et al.).

2.3 Vectors

This invention also provides vectors including a luciferase-encoding nucleotide sequence. As used herein, a vector is a nucleic acid molecule capable carrying a nucleic acid insert and of replicating in a cell. Vectors include, for example, plasmids, viruses, cosmids, transposons, and artificial chromosomes. Vectors typically comprise an origin of replication (e.g., bacterial or eukaryotic (mammalian)), a selectable marker and a cloning site (e.g., a multiple cloning site).

Examples of specific vectors that may be useful in the practice of the present invention include, but are not limited to, *E. coli* bacteriophages, for example, lambda derivatives, or plasmids, for example, pBR322 derivatives or pUC plasmid derivatives; phage DNAs, e.g., the numerous derivatives of phage 1, e.g., NM989, and other phage DNA, e.g., M13 and filamentous single stranded phage DNA; yeast vectors such as the 2μ plasmid or derivatives thereof; vectors useful in eukaryotic cells, for example, vectors useful in insect cells, such as baculovirus vectors, vectors useful in mammalian cells such as retroviral vectors, adenoviral vectors, adenovirus viral vectors, adeno-associated viral vectors, lentivirus vectors, SV40 viral vectors, herpes simplex viral vectors and vaccinia viral vectors; vectors derived from combinations of plasmids and phage DNAs, plasmids that have been modified to employ phage DNA or other expression control sequences; and the like.

This invention contemplates vectors comprising an expression construct that includes a luciferase-encoding nucleotide sequence. This invention also contemplates vectors (referred to herein as "empty vectors") comprising a luciferase-encoding nucleotide sequence that is not operably linked with a promoter or either or both of a 5' or 3' untranslated expression control sequence and that is positioned in the vector relative to a cloning site such that an expression control sequence inserted into the cloning site becomes operably linked with the luciferase-encoding nucleotide sequence. Accordingly, this invention provides empty vectors in a cloning site is positioned either upstream or downstream of the luciferase in the coming nucleotide sequence. Such vectors are configured to allow insertion of expression control sequences either or both of upstream or downstream of the luciferase encoding nucleotide sequence and operably linked to it. For example, a promoter and or a 5' UTR sequence can be cloned into the vector upstream of the luciferase encoding nucleotide sequence and any 3' UTR sequence can be introduced downstream of the gene. In certain embodiments, the expression construct comprises a promoter for the ACTB gene that includes a 5' UTR operably linked with a luciferase sequence of this invention. In certain embodiments, the promoter for the RPL10 gene can be used to control the expression of a luciferase gene operably linked to a 3'UTR sequence that is cloned downstream of luciferase. In particular, the promoter for the RPL10 gene may have the sequence of SEQ ID NO: 151 or the promoter can comprise at least nucleotides 150 to 200 of SEQ ID NO:151.

2.3.1 Plasmids

In certain embodiments, the vector is a plasmid. A variety of plasmids are known and are commercially available for use with luciferase, particularly for use in mammalian cell systems.

SwitchGear Genomics commercializes plasmid vectors that include a multiple cloning site comprising BglI, SacI, MluI, NheI, XhoI, BglII and Hind III cloning sites that can be operably linked with a luciferase-encoding gene of this invention, a polyA region, an origin of replication and an ampicillin resistance gene.

Promega commercializes the pGL-2, pGL-3 and pGL-4 luciferase reporter vectors. (See, e.g., www.promega.com/products/imaging-and-immunological-detection/in-vivo-imaging/pg14-in-vivo-imaging-vectors/.) Certain of these vectors include a Hind III cloning site, a luc2 gene, which can be replaced with a luciferase encoding nucleotide sequence of this invention, an SV40 late polyA region, an SV40 early enhancer/promoter, a neomycin resistance gene, synthetic Poly(A), an origin of replication, an ampicillin resistance gene, a synthetic poly(A) signal/transcription pause site and a CMV early enhancer promoter.

5. Recombinant Cells

A host cell that comprises the recombinant polynucleotide is referred to as a "recombinant cell." The gene is then expressed in the recombinant host cell to produce, e.g., a "recombinant polypeptide." A recombinant polynucleotide may serve a non-coding function. (e.g., promoter, origin of replication, ribosome-binding site, etc.) as well.

This invention also provides recombinant cells into which are transiently or stably introduced a vector of this invention. Nucleic acids can be introduced into cells by any methods known in the art, e.g., transfection or transduction by chemical or non-chemical means. The transfected cells can be adherent cells or cells in suspension.

This invention also provides a recombinant cell whose genome has been engineered to include the recombinant polynucleotide sequence. Genome engineering can be accomplished with zinc finger nucleases, site directed transposons, homologous recombination and other techniques available to those skilled in the art.

The cells used can be any of those desired by the practitioner. This includes prokaryotic or eukaryotic cells, including bacterial cells, mammalian cells, human cells and cell lines of any of these. The cells can be cultured cells.

Typically a recombinant cell having an expression construct of this invention will include expression control sequences, e.g. promoters, operable in that cell type.

6. Methods of Use

The luciferase nucleic acids of this invention are useful in reporter assays for activity of expression control sequences, in particular, of promoters.

In a typical assay and expression vector on this invention is introduced into a cell. The expression vector can comprise a luciferase-encoding nucleotide sequence operably linked to an expression control sequence of interest to the practitioner. For example, a recombinant cell can be provided having an expression construct in which the promoter is a biomarker for a biological pathway. The cells can be provided as a set in which each cell contains a different promoter.

The cells can be cultured alone or in parallel and/or with control cells. These cells can be cultured under different incubation conditions. For example, a different culture conditions can't involve exposure to a different test condition. A test condition can be any condition to which a cell is exposed. Test conditions include, for example, contacting the cell with a test composition, exposing the cell to a test environmental condition, over-expressing or knocking down expression of a particular gene of interest in the cell, or combinations of these.

A test compound can be any element or molecule, for example, small organic molecules and biopolymers. Drug candidates useful as test compositions in this invention include small organic molecules and biological molecules, e.g., biologics. Organic molecules used as pharmaceuticals generally are small organic molecules typically having a size up to about 5000 Da, up to about 2000 Da, or up to about 1000 Da. Organic biopolymers also are used as test compositions.

This invention contemplates a number of different types of assays. In one assay, a cell comprising an expression construct of this invention is exposed to a test condition and the activity of the expression control sequence is determined based on expression of the reporter sequence. In another assay, a expression control sequence for a single biological response is exposed to a plurality of different test conditions, e.g., a plurality of different test compositions, and the effect of each test condition on the activity of the expression control sequence is determined. This can be, for example, a high throughput assay in which tens, hundreds or thousands of conditions are tested.

In certain methods, the assay is multiplexed. A number of compounds, e.g., a library of compounds can be tested. This can involve testing each compound against a recombinant cell of this invention.

A container (e.g., a multiwell plate array) containing cells harboring an expression construct of this invention is useful for high-throughput screening of promoter activity. A cell comprising an expression construct that comprises a biological response biomarker promoter operably linked with a reporter gene is exposed to a test condition under conditions chosen by the operator. Cells in which the promoters are "turned on" will express the reporter sequences under their transcriptional control. The investigator then checks each well of the device to measure the amount of reporter transcribed. Generally, this involves measuring the signal produced by a reporter protein encoded by the reporter sequence.

Measuring a response includes quantitative and qualitative determinations. Qualitative measurement includes measuring a response or lack of response, regardless of intensity. A quantitative response generally involves measuring the intensity of a response.

For example, after incubation cells can be lysed and luciferase assay substrate is added. Then the amount of light generated is detected with a luminometer.

The choice of a proper detection system for a particular application is well within the abilities of one of skill in the art. Exemplary detection means include, but are not limited to, detection by unaided eye, light microscopy using the eye or an optical sensor as the detector, confocal microscopy, laser scanning confocal microscopy, imaging using quantum dot color, fluorescence spectrum or other quantum dot property and wide-field imaging with a 2D CCD camera. In an exemplary embodiment, the device is a luminescent plate reader. For example, the assay can be performed in a multiwell plate, e.g., a plate with multiples of 96 wells (e.g., 96-well plate, 384-well plate, 1536-well plate). In assays in which the reporter is luminescent or fluorescent molecule, the reporter may have to be induced to produce light. Commercially available microplate luminometers can be used to detect the signal. These are available from, for example, Tecan, Molecular Devices and Berthold.

Assays can involve creation of a standard curve against which measurements are compared to quantify the amount of expression.

It also can be useful to identify differences in transcription regulatory sequence activity in two cell types. For example gene expression differs when cells transform from normal to cancerous. Promoters that are overactive in cancer cells may be targets of pharmacological intervention. The arrays of this invention are useful to identify such transcription regulatory sequences. Accordingly, the investigator provides two sets of arrays comprising expression constructs in the wells. Once cell type is used for transformation in a first device and a second cell type, for transformation in a second device. The expression of reporter sequences between the two devices is compared to identify those expressed differently in the two cell types.

Using expression constructs in which the transcription regulatory sequences are operably linked to unique reporter sequences opens the possibility of performing tests without the use of multiwell plates. In such situations a single culture of cells contains the entire expression library distributed among the cells. The culture can be incubated under conditions chosen by the investigator. Then the expression products are isolated. Reporters that emit different colors can be used. As described, if the reporter is a barcode, because each expression vector has a unique nucleotide sequence tag or barcode associated with its partner nucleic acid segment, the amount of each of the reporter sequences can be measured by measuring the amount of transcript comprising each unique sequence. For example, the molecules can be detected on a DNA array that contains probes complementary to the unique sequences. The amount of hybridization to each probe indicates the amount of the reporter sequence expressed, which, in turn, reflects the activity of the transcription regulatory sequences.

EXAMPLES

Example 1

From a parental *Renilla* cDNA sequence, a semi-random library of different cDNAs were created representing different codon variants of the same protein coding sequence. A specific list of regulatory motifs and restriction sites were also excluded from these codon variant sequences (see Table 1).

Each of these codon variant cDNAs was cloned into an expression vector using the human beta actin promoter to drive expression of the cDNA. 94 random clones were picked from this variant library, the plasmids were purified, and 50 ng of each plasmid was then transiently transfected into human HT1080 cells to measure the level of expression of the codon variants. Each clone was then sequence verified in both directions to identify the sequence of the *Renilla* cDNA that was assayed in the transient reporter assay. The results of the functional screen are shown in FIG. 1.

The sequence of the highest expressing codon variant, labeled "RenS", is shown below. To measure various biological responses with reporter assays, it is often useful to include a protein degradation sequences such as the PEST sequence to decrease the half-life of the reporter protein. We also show below the sequence of RenS fused with the PEST domain, labeled "RenSP".

Example 2

To determine the relative brightness of RenSP compared to hRlucP, another humanized form of the *Renilla* luciferase, the RenSP and hRlucP genes were cloned into separate vectors each containing the human RPL10 promoter. Three independent plasmid purifications were conducted for each vector, and 50 ng of each plasmid was transfected with FuGENE HID in triplicate in human HT1080 cells in 96-well format. After 24 hours of incubation, 100 uL of LightSwitch Reagent (SwitchGear Genomics, Menlo Park, Calif.) was added to each well and incubated for 30 minutes before being read for 2 seconds on an Lmaxll-384 luminometer. These results show that RenSP is significantly brighter than hRlucP.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A nucleic acid molecule comprising a reporter nucleotide sequence encoding a polypeptide comprising a *Renilla* luciferase amino acid sequence having at least 99% sequence identity with SEQ ID NO:1, wherein the *Renilla* luciferase amino acid sequence is encoded by a luciferase nucleotide sequence having at least 95% sequence identity with SEQ ID NO:2.

2. The nucleic acid molecule of claim 1 wherein the *Renilla* luciferase amino acid sequence is encoded by a luciferase nucleotide sequence having at least 98% sequence identity with SEQ ID NO:2.

3. The nucleic acid molecule of claim 1 wherein the *Renilla* luciferase amino acid sequence is encoded by a luciferase nucleotide sequence having at least 99% sequence identity with SEQ ID NO:2.

4. The nucleic acid molecule of claim 1 wherein the *Renilla* luciferase amino acid sequence is encoded by a luciferase nucleotide sequence having at least 99.9% sequence identity with SEQ ID NO:2.

5. The nucleic acid molecule of claim 1 wherein the *Renilla* luciferase amino acid sequence is encoded by a luciferase nucleotide sequence identical with SEQ ID NO:2.

6. The nucleic acid molecule of claim 1 wherein the polypeptide is *Renilla* luciferase (SEQ ID NO:1) (RenS).

7. The nucleic acid molecule of claim 6 wherein RenS is encoded by the nucleotide sequence of SEQ ID NO:2.

8. The nucleic acid molecule of claim 1 wherein the polypeptide is a fusion protein comprising the *Renilla* luciferase amino acid sequence of SEQ ID NO:1.

9. The nucleic acid molecule of claim 8 wherein the *Renilla* luciferase amino acid sequence is encoded by the nucleotide sequence of SEQ ID NO:2.

10. The nucleic acid molecule of claim 8 wherein the fusion protein is RenSP (SEQ ID NO: 3).

11. The nucleic acid of claim 10 wherein the RenSP is encoded by the nucleotide sequence of SEQ ID NO: 4.

12. The nucleic acid molecule of claim 8 wherein the fusion polypeptide comprises a protein destabilization domain that decreases the half-life of *Renilla* luciferase.

13. The nucleic acid molecule of claim 1 wherein the luciferase nucleotide sequence contains no more than 10 regulatory motifs selected from the motifs of FIG. 3.

14. A recombinant nucleic acid comprising a promoter operably linked with a reporter nucleotide sequence, wherein the reporter nucleotide sequence encodes a polypeptide comprising a *Renilla* luciferase amino acid sequence having at least 99% sequence identity with SEQ ID NO:1, wherein the *Renilla* luciferase amino acid sequence is encoded by a luciferase nucleotide sequence having at least 95% sequence identity with SEQ ID NO:2.

15. The recombinant nucleic acid of claim 14 wherein the polypeptide comprises *Renilla* luciferase (SEQ ID NO:1) (RenS) encoded by a luciferase nucleotide sequence having at least 99% sequence identity with SEQ ID NO:2.

16. The recombinant nucleic acid of claim 14 wherein the *Renilla* Luciferase amino acid sequence is encoded by the luciferase nucleotide sequence of SEQ ID NO:2.

17. The recombinant nucleic acid of claim 14 wherein the polypeptide is RenSP (SEQ ID NO: 3).

18. The recombinant nucleic acid of claim 14 comprised in a plasmid.

19. A recombinant cell comprising a recombinant nucleic acid comprising a promoter operably linked with a reporter nucleotide sequence, wherein the reporter nucleotide sequence encodes a polypeptide comprising a *Renilla* luciferase amino acid sequence having at least 99% sequence identity with SEQ ID NO:1, wherein the *Renilla* luciferase amino acid sequence is encoded by a luciferase nucleotide sequence having at least 95% sequence identity with SEQ ID NO:2.

20. The recombinant cell of claim 19 wherein the polypeptide comprises *Renilla* luciferase (SEQ ID NO:1) (RenS) encoded by a luciferase nucleotide sequence having at least 99% sequence identity with SEQ ID NO:2.

21. The recombinant cell of claim 19 wherein the luciferase nucleotide sequence has at least 98% sequence identity with SEQ ID NO:2.

22. The recombinant cell of claim 19 wherein the luciferase nucleotide sequence is SEQ ID NO:2.

23. The recombinant cell of claim 19 which is a mammalian cell.

24. A kit comprising: (1) a vector containing a nucleic acid molecule comprising a reporter nucleotide sequence encoding a polypeptide comprising a *Renilla* luciferase amino acid sequence having at least 99% sequence identity with SEQ ID NO:1, wherein the *Renilla* luciferase amino acid sequence is encoded by a luciferase nucleotide sequence having at least 95% sequence identity with SEQ ID NO:2; and (2) a luciferase substrate.

25. The kit of claim 24 wherein the polypeptide comprises *Renilla* luciferase (SEQ ID NO:1) (RenS) encoded by a luciferase nucleotide sequence having at least 99% sequence identity with SEQ ID NO:2.

26. The kit of claim 24 wherein the luciferase nucleotide sequence has at least 98% sequence identity with SEQ ID NO:2.

27. The kit of claim 24 wherein the luciferase nucleotide sequence is SEQ ID NO:2.

28. The kit of claim 24 wherein the Luciferase substrate is coelenterazine.

29. The nucleic acid molecule of claim 1 further comprising a cloning site positioned relative to the reporter nucleotide sequence such that an expression control sequence inserted into the cloning site becomes operably linked with the luciferase-encoding nucleotide sequence.

30. The nucleic acid molecule of claim 1, wherein the *Renilla* luciferase amino acid sequence is SEQ ID NO:1.

31. The nucleic acid molecule of claim 2, wherein the *Renilla* luciferase amino acid sequence is SEQ ID NO:1.

32. The nucleic acid molecule of claim 3, wherein the *Renilla* luciferase amino acid sequence is SEQ ID NO:1.

33. The nucleic acid molecule of claim 4, wherein the *Renilla* luciferase amino acid sequence is SEQ ID NO:1.

34. The nucleic acid molecule of claim 13, wherein the *Renilla* luciferase amino acid sequence is SEQ ID NO:1.

35. The recombinant nucleic acid of claim 14, wherein the *Renilla* luciferase amino acid sequence is SEQ ID NO:1.

36. The recombinant cell of claim 19, wherein the *Renilla* luciferase amino acid sequence is SEQ ID NO:1.

37. The recombinant cell of claim 21, wherein the *Renilla* luciferase amino acid sequence is SEQ ID NO:1.

38. The recombinant cell of claim 23, wherein the *Renilla* luciferase amino acid sequence is SEQ ID NO:1.

39. The kit of claim 24, wherein the *Renilla* luciferase amino acid sequence is SEQ ID NO:1.

40. The kit of claim 26, wherein the *Renilla* luciferase amino acid sequence is SEQ ID NO:1.

41. The kit of claim 28, wherein the *Renilla* luciferase amino acid sequence is SEQ ID NO:1.

* * * * *